United States Patent
Yokobayashi et al.

(10) Patent No.: US 8,853,654 B2
(45) Date of Patent: Oct. 7, 2014

(54) SHIELD STRUCTURE FOR ELECTRON BEAM STERILIZATION EQUIPMENT

(71) Applicants: Takayasu Yokobayashi, Osaka (JP); Satoshi Ogawa, Osaka (JP); Toru Hosokawa, Osaka (JP)

(72) Inventors: Takayasu Yokobayashi, Osaka (JP); Satoshi Ogawa, Osaka (JP); Toru Hosokawa, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 0 days.

(21) Appl. No.: 14/351,177

(22) PCT Filed: Oct. 15, 2012

(86) PCT No.: PCT/JP2012/076576
§ 371 (c)(1),
(2), (4) Date: Apr. 11, 2014

(87) PCT Pub. No.: WO2013/058204
PCT Pub. Date: Apr. 25, 2013

(65) Prior Publication Data
US 2014/0231673 A1 Aug. 21, 2014

(30) Foreign Application Priority Data
Oct. 17, 2011 (JP) ................. 2011-227762

(51) Int. Cl.
| | | |
|---|---|---|
| A61L 2/08 | (2006.01) |
| A61L 2/00 | (2006.01) |
| A23B 9/06 | (2006.01) |
| B65B 55/02 | (2006.01) |
| B65B 55/08 | (2006.01) |

(52) U.S. Cl.
CPC ....................................... *A61L 2/00* (2013.01)
USPC ............... 250/492.3; 250/492.1; 250/455.11; 53/111 R; 422/1; 141/69

(58) Field of Classification Search
USPC ........ 250/491.1, 492.1, 492.3, 505.1, 453.11, 250/454.11, 455.11; 53/425, 426, 111 R, 53/281; 422/1, 62, 308; 141/11, 69; 436/1
See application file for complete search history.

(56) References Cited

U.S. PATENT DOCUMENTS 7,641,851 B2 * 1/2010 Williams et al. ................ 422/22
8,022,375 B2 * 9/2011 Williams et al. ........... 250/486.1
(Continued)

FOREIGN PATENT DOCUMENTS

| | | |
|---|---|---|
| EP | 2316495 | 5/2012 |
| JP | 2008-230667 | 10/2008 |

(Continued)

OTHER PUBLICATIONS

Machine translation of JP 2009-126703.
(Continued)

Primary Examiner — Bernard E Souw
(74) Attorney, Agent, or Firm — Fildes & Outland, P.C.

(57) ABSTRACT

A shield structure for electron beam sterilization equipment. The shield structure satisfies at least one of the following conditions: (I) an outer diameter D4 of an internal circumferential shield S4 is larger than an outer diameter D5 of an internal circumferential shield S5, and (II) an internal circumferential shield ST2 of a circular path LT2 downstream of an entrance trap zone Z1 connected to an outer-surface sterilization zone Z2 has an outer diameter DT2 that is larger than an outer diameter D1 of an internal circumferential shield S1 of a circular path L1 upstream of the outer-surface sterilization zone Z2.

5 Claims, 17 Drawing Sheets

(56) References Cited

U.S. PATENT DOCUMENTS

| | | | |
|---|---|---|---|
| 8,294,126 B2* | 10/2012 | Humele et al. | 250/492.3 |
| 8,379,209 B2* | 2/2013 | Yokobayashi et al. | 356/437 |
| 8,461,550 B2* | 6/2013 | Nishino et al. | 250/455.11 |
| 8,501,262 B2* | 8/2013 | Bird et al. | 426/549 |
| 8,586,944 B2 | 11/2013 | Avnery | |
| 8,618,503 B2* | 12/2013 | Nishino et al. | 250/455.11 |
| 2008/0193341 A1* | 8/2008 | Fontcuberta et al. | 422/186 |
| 2009/0110613 A1* | 4/2009 | Naka et al. | 422/186 |
| 2012/0251386 A1* | 10/2012 | Wootton et al. | 422/26 |
| 2013/0182363 A1* | 7/2013 | Kobayashi et al. | 361/215 |
| 2013/0283733 A1* | 10/2013 | Py | 53/425 |
| 2014/0029007 A1* | 1/2014 | Yokobayashi et al. | 356/437 |

FOREIGN PATENT DOCUMENTS

| | | |
|---|---|---|
| JP | 2008-296955 | 12/2008 |
| JP | 2009-35330 | 2/2009 |
| JP | 2009-126703 | 6/2009 |
| JP | 2009-526971 | 7/2009 |
| JP | 2011-93567 | 5/2011 |

OTHER PUBLICATIONS

Machine translation of JP 2008-230667.

International Search Report issued in International application No. PCT/JP2012/076576.

* cited by examiner

SHIELD STRUCTURE FOR ELECTRON BEAM STERILIZATION EQUIPMENT

TECHNICAL FIELD

The present invention relates to a shield structure for electron beam sterilization equipment that sterilizes containers and instruments for foods, chemical solutions, and so on by electron radiation.

BACKGROUND ART

When electron beams (cathode rays) emitted for sterilizing cellular microorganisms collide with metallic shields (containing lead) disposed as shields, the electron beams are attenuated and then are reflected and diffracted as X-rays in a widely diffused state. For example, if electron beams collide with the shield three or four times, although depending on the intensity thereof, X-rays can be attenuated to a degree of intensity that does not affect a human body.

For example, if an electron beam irradiation nozzle is inserted into the inlet of a container to sterilize the inner surface of the container, electron beams are emitted from the entire periphery of the electron beam irradiation nozzle. If a revolving transport device that is a rotary device stored in a shield chamber is used to continuously sterilize the container at a high speed, the container is sterilized with the electron beam irradiation nozzle inserted into the inlet, the electron beam irradiation nozzle being revolved with the container. In this case, an electron beam generator cannot turn on or off electron radiation because a high voltage is supplied, leading to continuous radiation. Thus, electron beams (X-rays) leaking from the entrance or exit of the container formed on the shield chamber may be seriously shielded or attenuated.

For example, patent literature 1 is proposed as a technique of sterilizing the inner surface of a container with an electron beam irradiation nozzle inserted into the inlet of the container. Patent literature 2 proposes the layout of an electron beam irradiation nozzle for sterilizing an inner surface and an electron beam irradiator for sterilizing an outer surface.

CITATION LIST

Patent Literatures

Patent Literature 1: National Publication of International Patent Application No. 2009-526971
Patent Literature 2: Japanese Patent Laid-Open No. 2009-35330 (FIGS. 9, 10, 13, 15, 16)

SUMMARY OF INVENTION

Technical Problem

In Patent Literature 1, however, the configuration of the electron beam irradiation nozzle is proposed but a shield is not described.

In Patent Literature 2, the electron beam irradiator is disposed with the electron beam irradiation nozzle but a shield is not specifically described.

An object of the present invention is to solve the problem and provide a shield structure for electron beam sterilization equipment that can reliably attenuate the leakage of X-rays so as not to adversely affect a human body.

Solution to Problem

The first aspect of the present invention is a shield structure for electron beam sterilization, the shield structure including: a plurality of shield chambers (R1-R3) each containing each one of a plurality of circular paths (L1-L3) connected in series; wherein containers are transported along with the circular paths; and a sterilization zone (Z2, Z3) including an outer-surface sterilization zone (Z2) in which the outer surface of a container (B) is sterilized by emitting electron beams to the container (B) from electron beam irradiators (E1, E2) disposed outside first and second circular paths (L1, L2) upstream in a container transporting direction, and an inner-surface sterilization zone (Z3) in which an electron beam irradiation nozzle (En) is inserted into the container (B) transported along a third circular path (L3) downstream, and thereby electron beams are emitted to sterilize an inner surface of the container (B), wherein the sterilization zone (Z2, Z3) has a container entrance (P0-1) where an entrance trap zone (Z1) for attenuating electron beams is connected and a container exit (P3-4) where an exit trap zone (Z4) for attenuating electron beams is connected, at least one of the entrance trap zone (Z1) and the exit trap zone (Z4) includes more than two of the plurality of circular paths connected in series, and two or more of the plurality of shield chambers containing the respective two or more of the plurality of circular paths, a sterilization zone internal circumferential shield (S1, S2, S3) composed of a metallic shield is mounted along the internal circumference of each of the circular paths (L1-L3) in the sterilization zone (Z2, Z3), a trap zone internal circumferential shield (S4, S5) (ST1, ST2) composed of a metallic shield is mounted on two or more of the plurality of the circular paths (L4) (LT2) in the entrance trap zone (Z1) and/or the exit trap zone (Z4) (LT2), along the internal circumference of the circular paths (L4, L5) (LT1, LT2), and the shield structure satisfies at least one of the conditions (I) and (II):

(I) the circular paths in the exit trap connected to the inner-surface sterilization zone include a first upstream circular path and a first downstream circular path connected to the first upstream circular path, and the internal circumferential shield (S5) of the first downstream circular path (L5) has an outer diameter (D5) larger than an outer diameter (D4) of the internal circumferential shield (S4) of the first downstream circular path (L4), (II) the circular paths in the entrance trap zone connected to the outer-surface sterilization zone include a second upstream circular path and a second downstream circular path connected to the second upstream circular path, and the internal circumferential shield (ST2) of the second downstream circular path (LT2) has a larger outer diameter (DT2) than an outer diameter (D1) of the internal circumferential shield (S1) of the second upstream circular path (L1).

The second aspect of the present invention is the configuration according to the first aspect, wherein the internal circumferential shield (S5) of the first downstream circular path (L5) has an outer diameter (D5) 1.3 to 2.5 times larger than the outer diameter (D4) of the internal circumferential shield (S4) of the first upstream circular path (L4) in the exit trap zone (Z4).

The third aspect of the present invention is the configuration according to the first aspect, wherein the internal circumferential shield (ST2) of the second downstream circular path (LT2) has an outer diameter (DT2) 1.3 to 2.5 times larger than the outer diameter (D1) of the internal circumferential shield (S1) of the second upstream circular path (L1) in the entrance trap zone.

The fourth aspect of the present invention is the configuration according to the first aspect, wherein in the exit trap zone (Z4), a first shield chamber (R4) containing a most upstream circular path (L4) has a first attenuating chamber (R4b) opened to the container exit (P3-4) of the inner-surface sterilization zone, the first attenuating chamber (R4b) being formed by dividing the first shield chamber (R4) by a first trap wall (T4) protruding forward to the container exit (P3-4) from a shield wall of the first shield chamber opposed to the container exit (P3-4).

The fifth aspect of the present invention is the configuration according to the first aspect, wherein in the outer-surface sterilization zone (Z2), a second shield chamber (R2) containing a most downstream circular path (L2) has a second attenuating chamber (R2b) opened to the container entrance (P2-3) of the inner-surface sterilization zone, the second attenuating chamber (R2b) being formed by dividing the second shield chamber (R2) by a second trap wall (T2) protruding forward to the container entrance (P2-3) from a shield wall of the second shield chamber opposed to the container entrance (P2-3).

The reference numerals are identical to those of embodiments.

Advantageous Effects of Invention

According to the first aspect of the present invention, the internal circumferential shield is mounted along the internal circumference of the revolving channel in the sterilization zone. Thus, the number of reflections of electron beams is increased between the shield chambers and the internal circumferential shields, achieving effective attenuation. Moreover, electron beams (X-rays) leaking from the container entrance and the container exit of the shield chamber in the sterilization zone can be effectively blocked by the internal circumferential shields disposed in a trap zone. This can effectively attenuate electron beams (X-rays) leaking upstream and downstream.

In condition (I), a sufficient transport distance and time is necessary for the insertion of the electron beam irradiation nozzle and radiation. Thus, the revolving channel needs to be increased in length and diameter. As the revolving channel of the trap zone disposed at the container exit increases in diameter, the diameter of the revolving channel in the inner-surface sterilization zone is limited. Thus, the revolving channel cannot have a large diameter in the trap zone. This necessarily tends to increase an electron beam (X-ray) dose leaking from the container exit of the inner-surface sterilization zone to the shield chamber upstream of the trap zone. In order to address this problem, the outer diameter of the internal circumferential shield of the downstream revolving channel is set larger than that of the internal circumferential shield near the container exit. This can effectively block and reduce a dose of radiation leaking downstream from the upstream shield chamber.

In condition (II), the internal circumferential shield of the revolving channel downstream of the entrance trap zone connected to the container entrance of the outer-surface sterilization zone has a larger outer diameter than the internal circumferential shield of the revolving channel upstream of the outer-surface sterilization zone. This can effectively block and reduce an electron beam (X-ray) dose leaking from the inner-surface sterilization zone and the outer-surface sterilization zone through the container entrance.

According to the second aspect of the present invention, the outer diameter of the internal circumferential shield of the downstream revolving channel is 1.3 to 2.5 times larger than that of the internal circumferential shield near the container exit. Thus, the enhanced effect of blocking and reducing a dose of radiation leaking downstream from the upstream shield chamber can be obtained without excessively increasing the size of a facility.

According to the third aspect of the present invention, the internal circumferential shield of the revolving channel downstream of the entrance trap zone connected to the container entrance of the outer-surface sterilization zone has an outer diameter 1.3 to 2.5 times larger than the outer diameter of the internal circumferential shield of the revolving channel upstream of the outer-surface sterilization zone. This can obtain the enhanced effect of blocking and reducing an electron beam (X-ray) dose leaking from the inner-surface sterilization zone and the outer-surface sterilization zone through the container entrance without excessively increasing the size of a facility.

According to the fourth aspect of the present invention, the trap wall is provided in the shield chamber upstream of the exit trap zone to form the attenuating chamber. Thus, electron beams (X-rays) leaking from the container exit of the inner-surface sterilization zone can be guided into the attenuating chamber by the trap wall. This can effectively reflect and attenuate electron beams (X-rays) in the attenuating chamber.

According to the fifth aspect of the present invention, in the outer-surface sterilization zone, the trap wall is formed in the shield chamber facing the container entrance, forming the attenuating chamber. Thus, electron beams (X-rays) leaking from the container entrance of the inner-surface sterilization zone can be introduced into the attenuating chamber by the trap wall and can be effectively reflected and attenuated in the attenuating chamber.

DESCRIPTION OF EMBODIMENTS

First Embodiment

A first embodiment of electron beam sterilization equipment for containers including a shield structure according to the present invention will be described below with reference to the accompanying drawings.

[Outline of Electron Beam Sterilization Equipment]

Figure 1:
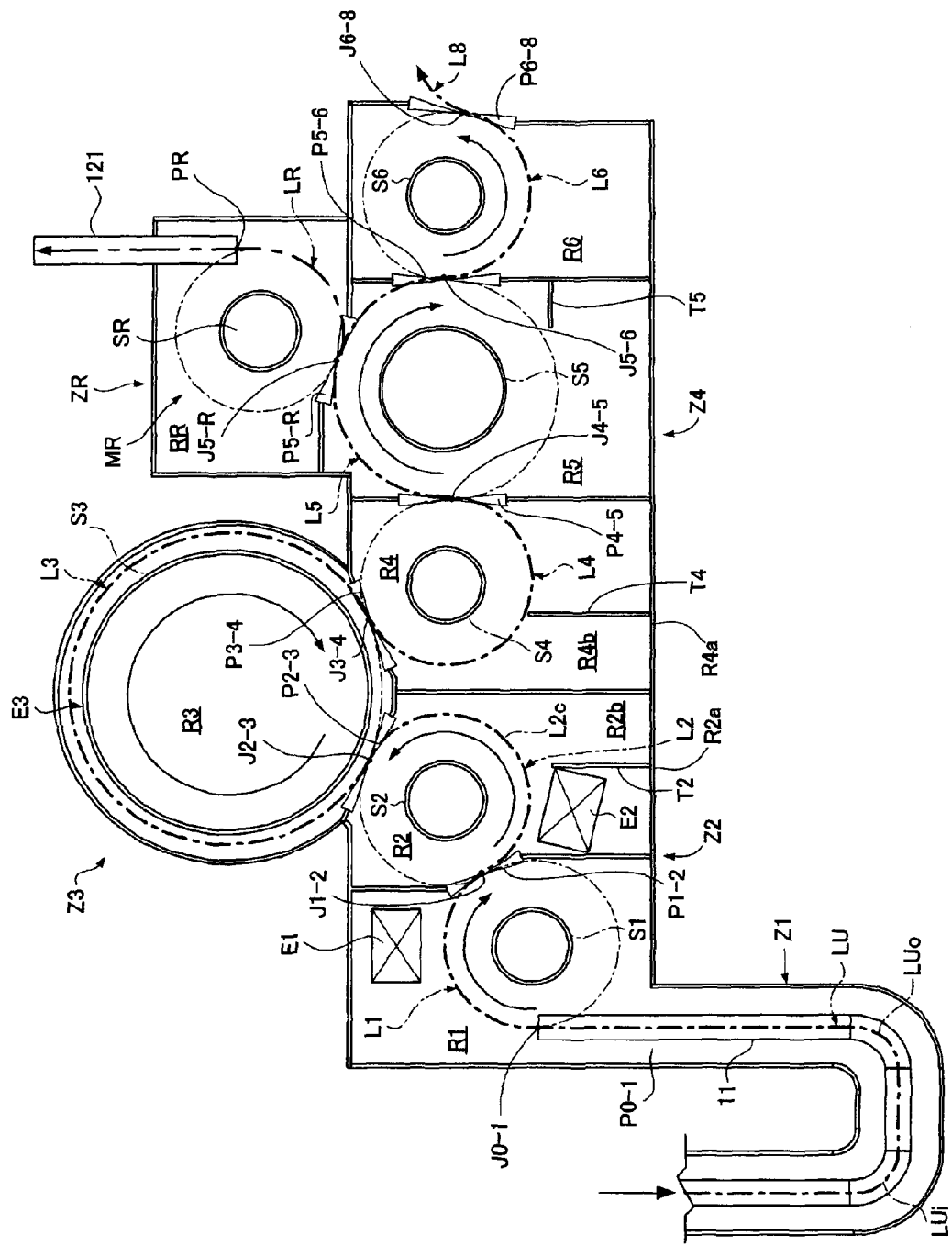
FIG. 1 is a plan view schematically showing a first embodiment of electron beam sterilization equipment according to the present invention.
Figure 2:
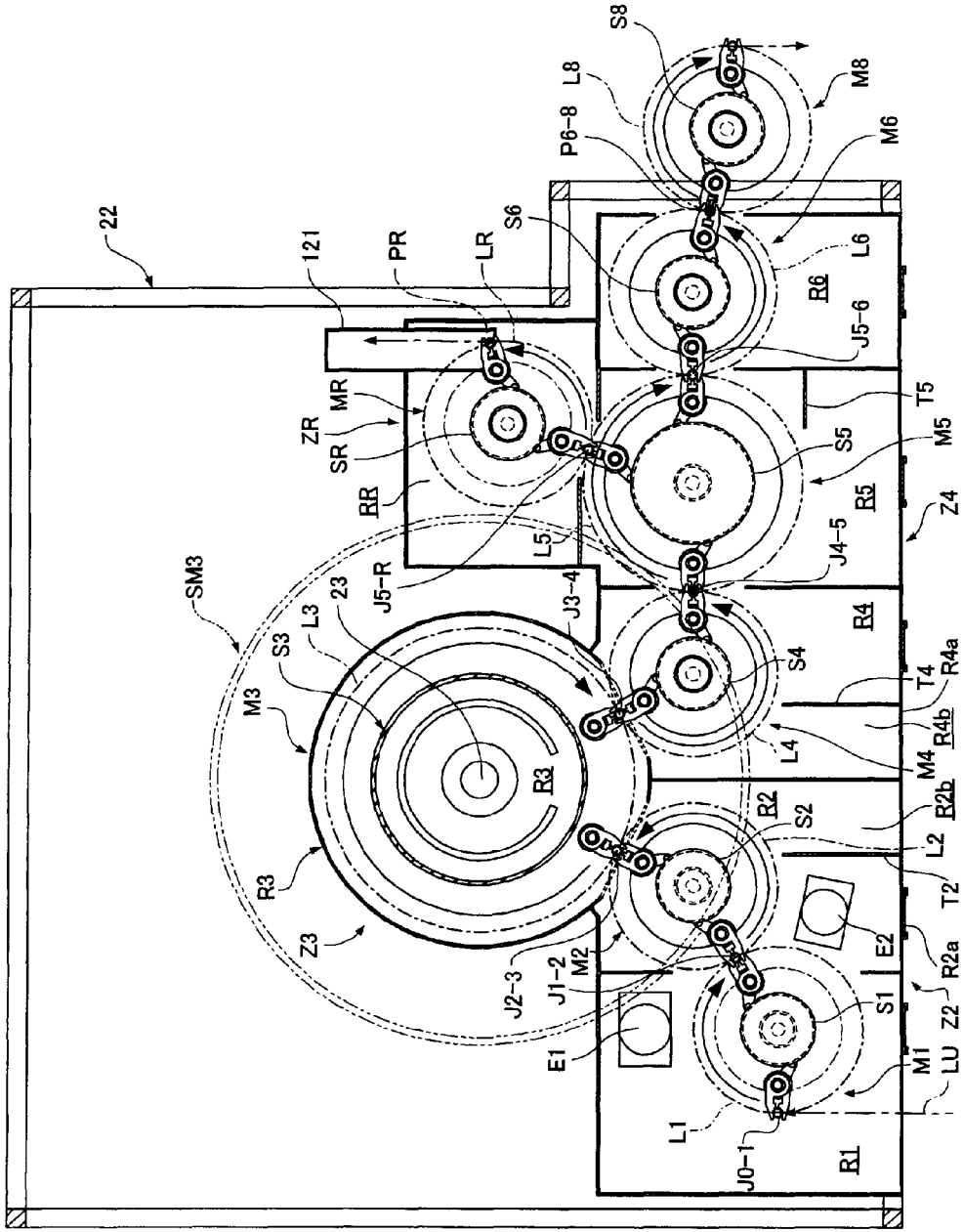
FIG. 2 is a cross section showing inner-surface and outer-surface sterilization zones and an exit trap zone in plan view.
Figure 3:
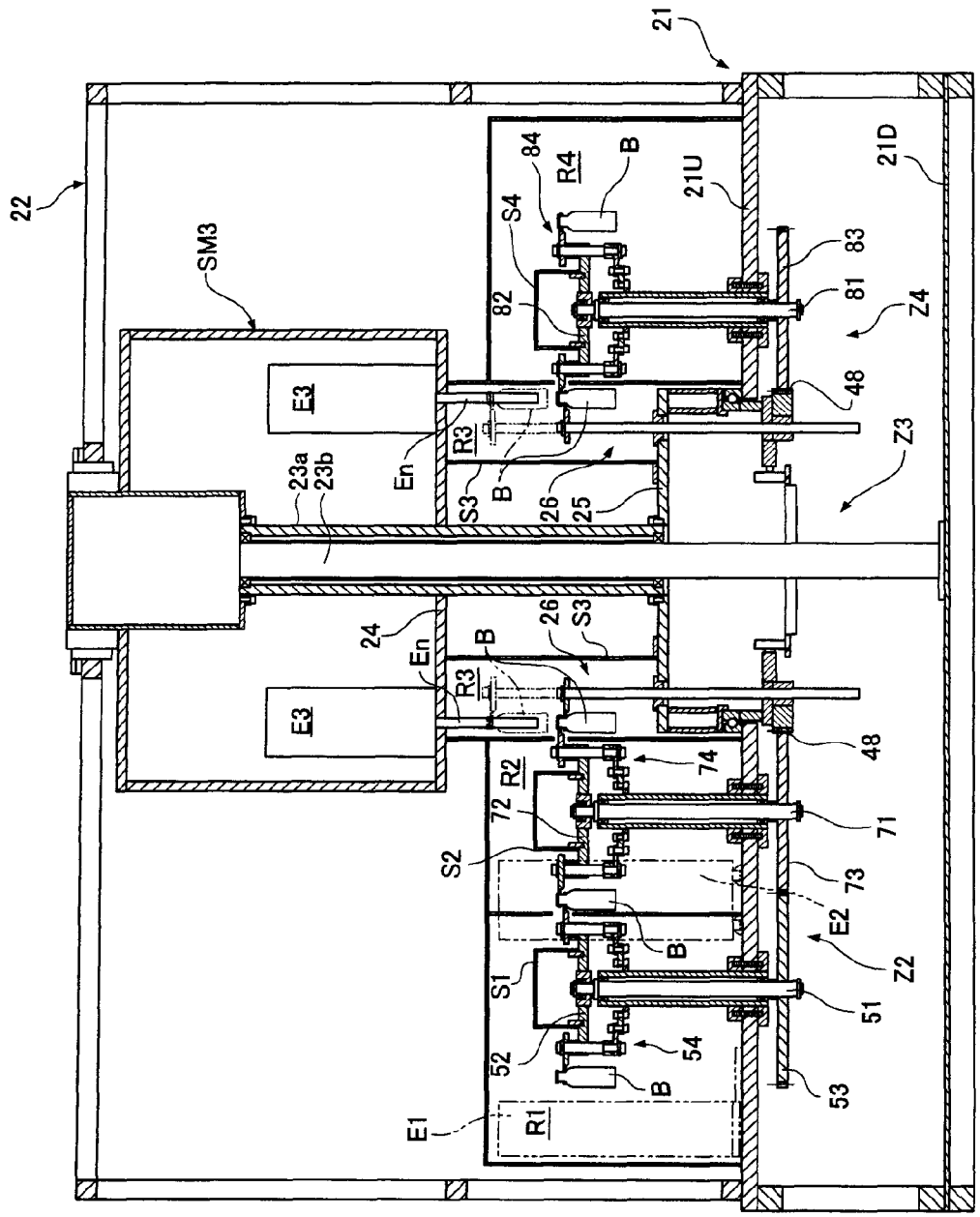
FIG. 3 is a longitudinal section showing the electron beam sterilization equipment, mainly the inner-surface sterilization zone.

As shown in FIGS. 1 to 3, electron beam sterilization equipment includes an entrance trap zone Z1, an outer-surface sterilization zone Z2, an inner-surface sterilization zone Z3, and an exit trap zone Z4. The entrance trap zone Z1 includes a U-shaped feed channel LU. The outer-surface sterilization zone Z2, the inner-surface sterilization zone Z3, and the exit trap zone Z4 are configured such that first to sixth revolving channels L1 to L6 for transporting containers B by means of first to sixth revolving conveyors M1 to M6 are connected in series. Furthermore, on the back of the exit trap zone Z4, a reject zone ZR is provided to transport insufficiently sterilized ones of the containers B along a reject revolving channel LR formed by a reject revolving conveyor MR and eject the transported containers B from a reject ejection port PR.

In the outer-surface sterilization zone Z2, the first and second revolving conveyors M1 and M2 forming the first and second circular paths L1 and L2 are connected in series and are respectively stored in first and second shield chambers R1 and R2 composed of metallic shields. The first shield chamber R1 contains a first electron beam irradiator E1 that sterilizes one outer half surface of the container B by electron beam irradiation when the container B held by the first revolving conveyor M1 via a neck n is transported along the first revolving channel L1. The second shield chamber R2 contains a second electron beam irradiator E2 that sterilizes the other outer half surface of the container B by electron beam irradiation when the container B held by the second revolving conveyor M2 via the neck n is transported along the second revolving channel L2.

In the inner-surface sterilization zone Z3, a third shield chamber R3 composed of a shield contains the third revolving conveyor M3 forming the third revolving channel L3. The third revolving conveyor M3 includes a plurality of container lifting/holding devices 26 spaced at regular intervals. The container lifting/holding devices 26 hold the containers B via the necks n and sequentially lift the transported containers B to insert electron beam irradiation nozzles En into the inlets of the containers B. Furthermore, third electron beam irradiators E3 that emit electron beams from the electron beam irradiation nozzles En hung is disposed on the container lifting/holding devices 26 respectively.

The fourth to sixth revolving conveyors M4 to M6 forming the fourth to sixth circular paths L4 to L6 are connected in series in the exit trap zone Z4. The fourth to sixth revolving conveyors M4 to M6 are respectively stored in fourth to sixth shield chambers R4 to R6 composed of shields. The fourth to sixth shield chambers R4 to R6 attenuate electron beams leaking from a 3-4 connecting opening (container exit) P3-4 and X-rays [hereinafter, will be called electron beams (X-rays)] generated by reflecting or diffracting electron beams to the metallic shields. In the fourth to sixth shield chambers R4 to R6, the containers B are held by the fourth to sixth revolving conveyors M4 to M6 via the necks n and are transported along the fourth to sixth circular paths L4 to L6.

The sixth revolving channel L6 is connected to an intermediate revolving channel L8 formed by an intermediate revolving conveyor M8. The intermediate revolving channel L8 is connected to a feeder (not shown) so as to fill the sterilized containers B with a liquid.

The reject zone ZR contains the reject revolving conveyor MR forming the reject revolving channel LR connected to the fifth revolving channel L5. The reject revolving conveyor MR is stored in a reject shield chamber RR surrounded by a shield.

[The Detail of the Electron Beam Sterilization Equipment]

The electron beam sterilization equipment is installed in a clean room 22 set on a base frame 21 via a structural frame. The first and second revolving conveyors M1 and M2 of the outer-surface sterilization zone Z2, the fourth to sixth revolving conveyors M4 to M6 of the exit trap zone Z4, and the reject revolving conveyor MR of the reject zone ZR are operated in a synchronized manner with respect to the third revolving conveyor M3 of the inner-surface sterilization zone Z3.

(Inner-Surface Sterilization Zone)

The third revolving conveyor M3 is set up by a main shaft 23b that is raised on a bottom frame 21D of the base frame 21 so as to penetrate a base top plate 21U. A support table 24 is supported on an outer cylindrical shaft 23a rotatably supported on the main shaft 23b, and a swiveling table 25 is supported under the outer cylindrical shaft 23a. The tables are rotated at a predetermined speed along a transport direction by a revolving transport drive unit 49 shown in FIG. 5. The support table 24 has a plurality of third electron beam generators E3 and electron beam irradiation nozzles En connected in a hanging position to the third electron beam generators E3. The third electron beam generators E3 and the electron beam irradiation nozzles En are spaced at regular intervals in a circumferential direction. Reference character SM3 denotes a third outer shield that shields the third electron beam generators E3 on the outer periphery and top surface of the support table 24.

Figures 4A, 4B:
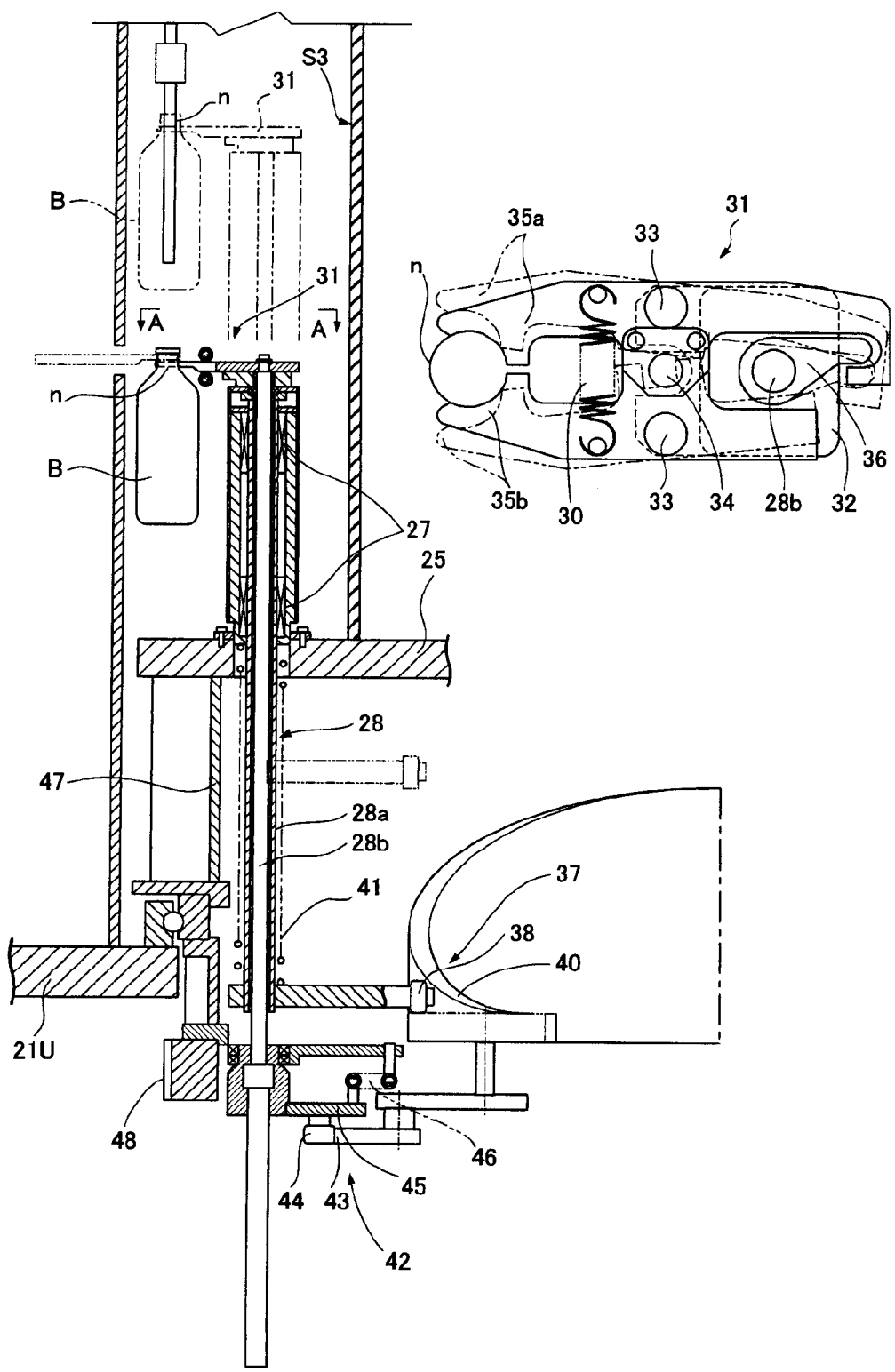
FIG. 4A is a longitudinal section of a container lifting/holding device.
FIG. 4B is a cross-sectional view taken along line A-A of FIG. 4A.

The container lifting/holding devices 26 opposed to the electron beam irradiation nozzles En are disposed at equal intervals in the circumferential direction on the outer periphery of the swiveling table 25. The container lifting/holding devices 26 hold the necks n to move up or down the containers B. As shown in FIGS. 4A and 4B, an actuator shaft 28 composed of a double cylinder penetrates the swiveling table 25. The actuator shaft 28 includes a hoisting/lowering outer shaft 28a that is disposed on the swiveling table 25 via a thrust bearing 27 so as to move up and down, and an opening/closing inner shaft 28b that is fit so as to rotate about an axis in the outer shaft 28a.

A clamp 31 that can hold the container B via the neck n is provided on the upper end of the outer shaft 28a, and a lifting cam mechanism 37 that moves up and down the clamp 31 is provided on the lower end of the outer shaft 28a.

As shown in FIG. 4B, the clamp 31 provided on the upper end of the outer shaft 28a is supported on a base plate 32 fixed on the outer shaft 28a so as to open and close a pair of clamp arms 35a and 35b via a pair of support pins 33. The clamp arm 35b is operated in synchronization with the clamp arm 35a via an interlock pin 34 fixed to the clamp arm 35a via a plate member, and the clamp arms 35a and 35b are urged in a holding direction by a coil spring 30 for closing and urging. Moreover, an opening/closing output cam 36 pivoted by the inner shaft 28b so as to open and close the clamp arm 35a is provided between the proximal ends of the clamp arms 35a and 35b.

The lifting cam mechanism 37 provided on the lower end of the outer shaft 28a has a lifting cam follower 38 that is supported via a lifting arm so as to lift the clamp 31 by rolling the cam surface of the lifting cam 40 mounted on the base frame 21. Reference numeral 41 denotes a lifting restraint spring that urges the lifting cam follower 38 to the cam surface of the lifting cam 40.

An opening/closing output cam 36 is attached to the upper end of the inner shaft 28b and an opening/closing input cam mechanism 42 for opening and closing the clamp 31 is provided on the lower end of the inner shaft 28b. The opening/closing input cam mechanism 42 has an opening/closing input cam follower 44 that rolls the cam surface of an opening/closing input cam 43 via an opening/closing input arm 45 on the inner shaft 28b. Reference numeral 46 denotes an opening/closing input restraint spring that urges the opening/closing input cam follower 44 to the cam surface of the opening/closing input cam 43.

The lifting cam 40 is disposed between a 2-3 joint J2-3 and a 3-4 joint J3-4 of the third revolving channel L3. The opening/closing input cam 43 is disposed from the upstream side of the 3-4 joint J3-4 to the downstream side of the 2-3 joint J2-3.

In this configuration, the container B is transferred via the neck n to the clamp arms 35a and 35b opened by an action of the opening/closing input cam 43 at the 2-3 joint J2-3 during the rotations of the swiveling table 25, and then the container B is transported with the neck n held by the closed clamp arms 35a and 35b. After that, the container B is lifted via the clamp 31 by an action of the lifting cam 40 so as to fit the electron beam irradiation nozzle En to the inlet of the container B. Moreover, the inner surface of the container B is sterilized by electron beams emitted from the electron beam irradiation nozzle En. Subsequently, the container B is moved down via the clamp arms 35a and 35b by an action of the lifting cam 40 so as to separate the electron beam irradiation nozzle En from the inlet. When the container B approaches the 3-4 joint J3-4, the clamp arms 35a and 35b are opened by an action of the opening/closing input cam 43 so as to transfer the container B to the fourth revolving channel L4 with the neck n transferred to the fourth revolving conveyor M4.

On the inner circumference of the third revolving channel L3, a third internal circumferential shield S3 is disposed between the swiveling table 25 and the support table 24.

Figure 5:
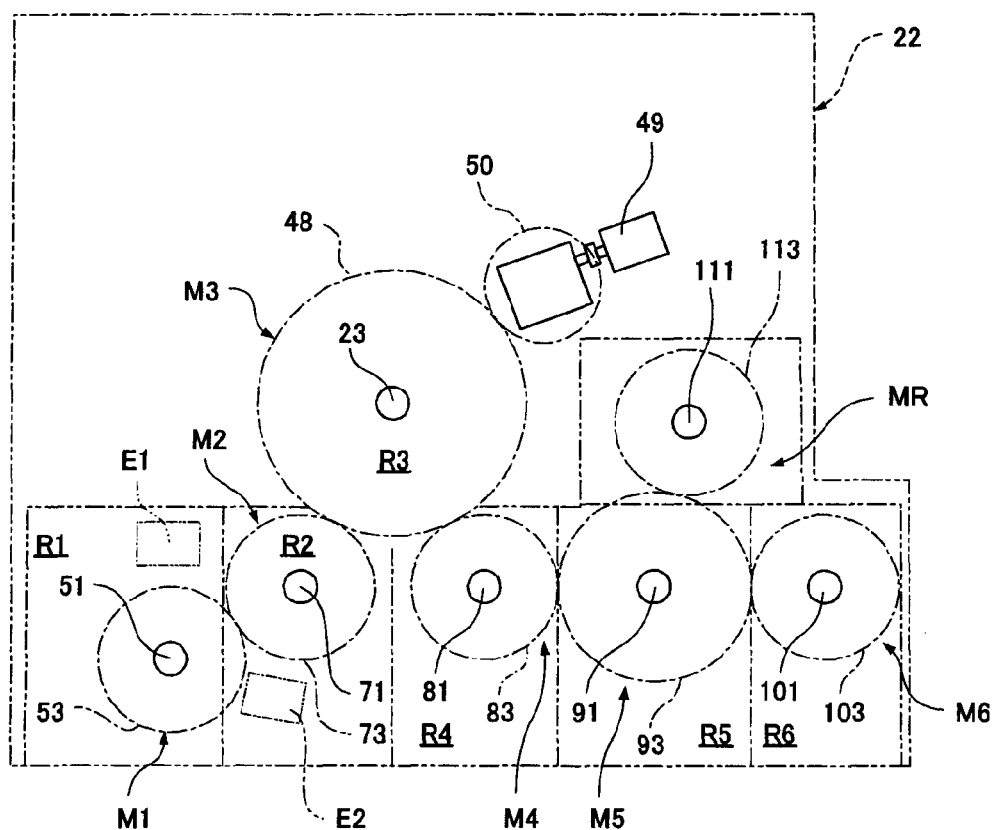
FIG. 5 is a plan view showing a driving system for first to sixth revolving conveyors and a reject revolving conveyor.

As shown in FIGS. 3, 4A, and 4B, an interlock third ring gear 48 is attached to an outer wall 47 that is hung downward from the outer periphery of the swiveling table 25 and is rotatably supported on the base top plate 21U via a ring bearing. As shown in FIG. 5, a conveyor drive gear 50 rotated by a revolving transport drive unit 49 via a speed reducer is engaged with the interlock third ring gear 48.

(Outer-Surface Sterilization Zone)

As shown in FIG. 3, the first and second revolving conveyors M1 and M2 are respectively installed in the first and second shield chambers R1 and R2 on the base top plate 21U. The first revolving conveyor M1 and the second revolving conveyor M2 include a first swiveling table 52 and a second swiveling table 72 fixed on the respective upper ends of a first rotating shaft 51 and a second rotating shaft 71 that rotatably penetrate the base top plate 21U via bearings. Furthermore, a second interlock gear 73 engaged with the interlock third ring gear 48 of the third revolving conveyor M3 is attached to the lower end of the second rotating shaft 71, and a first interlock gear 53 engaged with the second interlock gear 73 is attached to the lower end of the first rotating shaft 51. The first interlock gear 53 and the second interlock gear 73 are rotated while being interlocked with the outer cylindrical shaft 23a of the third revolving conveyor M3.

The outer peripheries of the first swiveling table 52 and the second swiveling table 72 have first and second container holders 54 and 74 spaced at regular intervals. In this case, the first and second container holders 54 and 74 are substantially identical in structure except for the holding position of the neck n. Thus, only the first container holder 54 will be discussed below, and the explanation of the second container holder 74 denoted by the same reference numerals is omitted. As will be discussed later, fourth to sixth container holders 84 and 94 in the exit trap zone Z4 and a reject container holder 114 in the reject zone ZR are substantially identical in configuration except for the holding position of the neck n, and the detailed explanation thereof is omitted.

Figure 6:
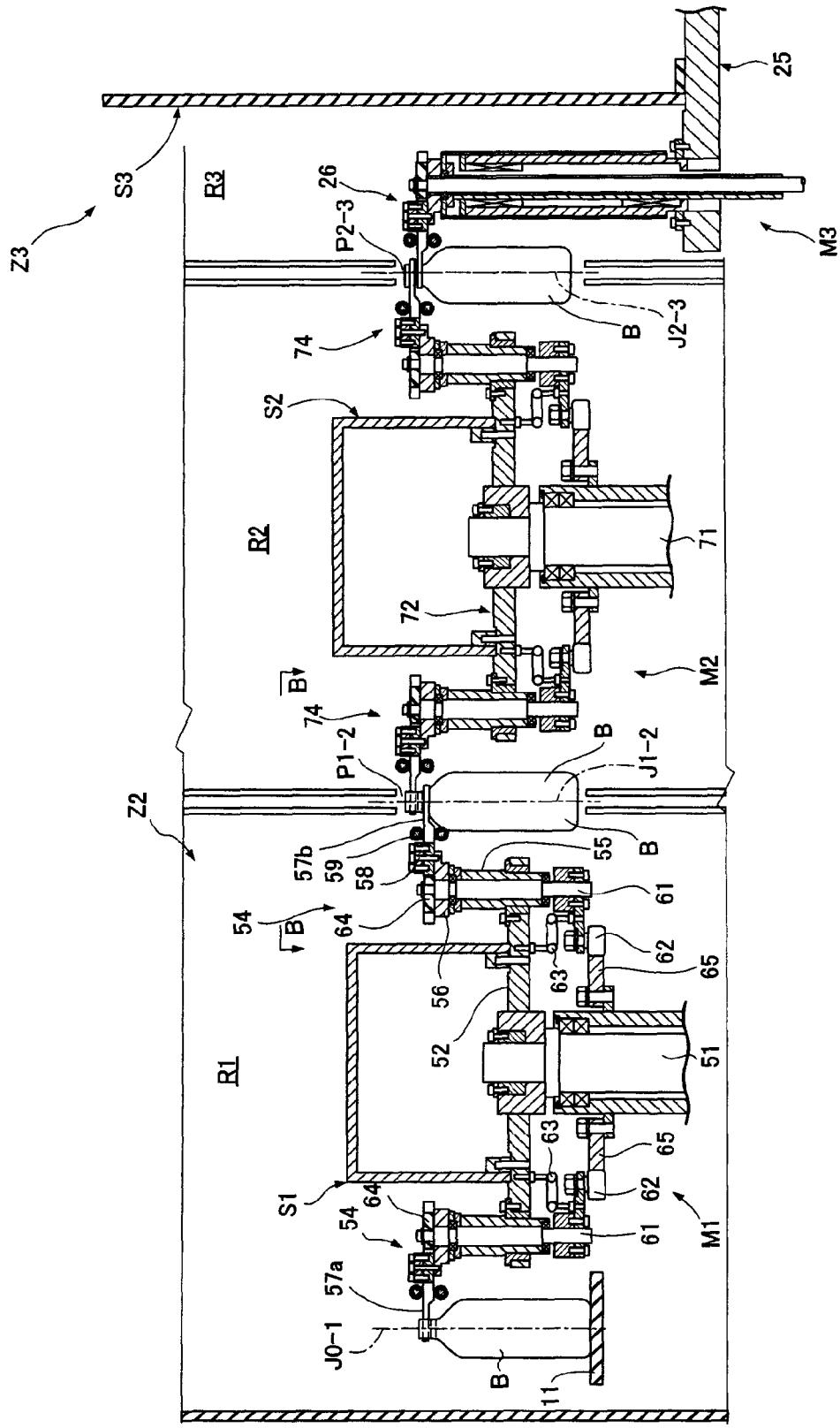
FIG. 6 is a longitudinal section showing the first and second revolving conveyors.
Figure 7:
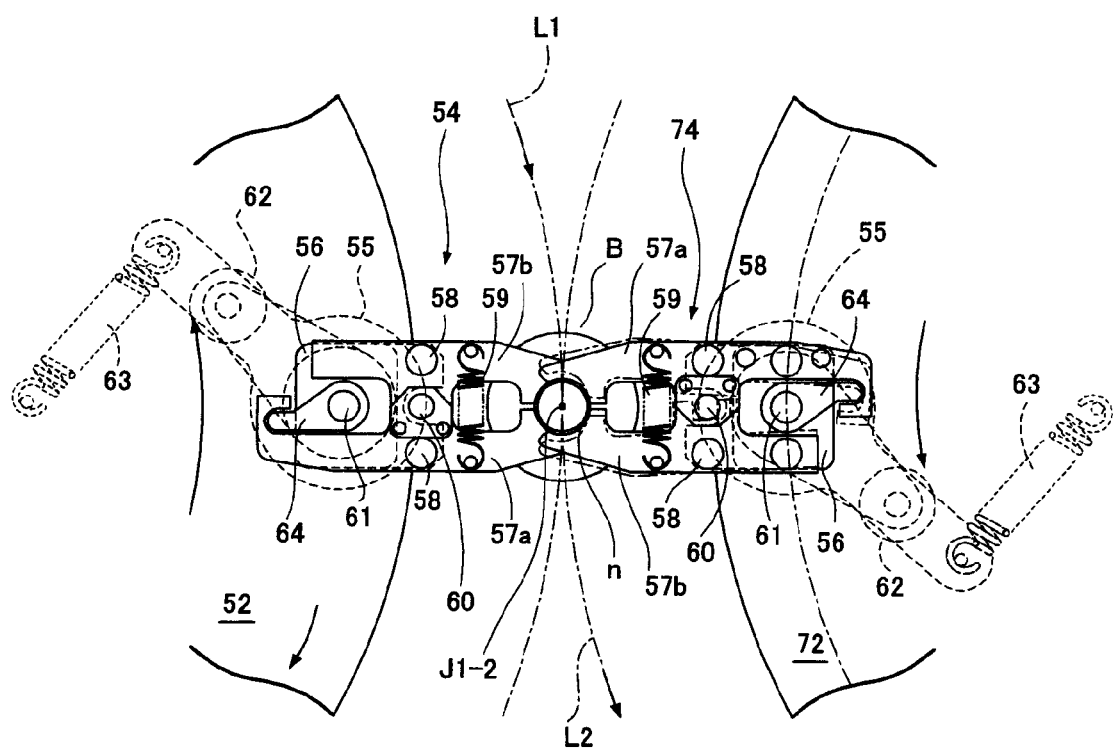
FIG. 7 is a cross-sectional view taken along line B-B of FIG. 6.
Figure 8:
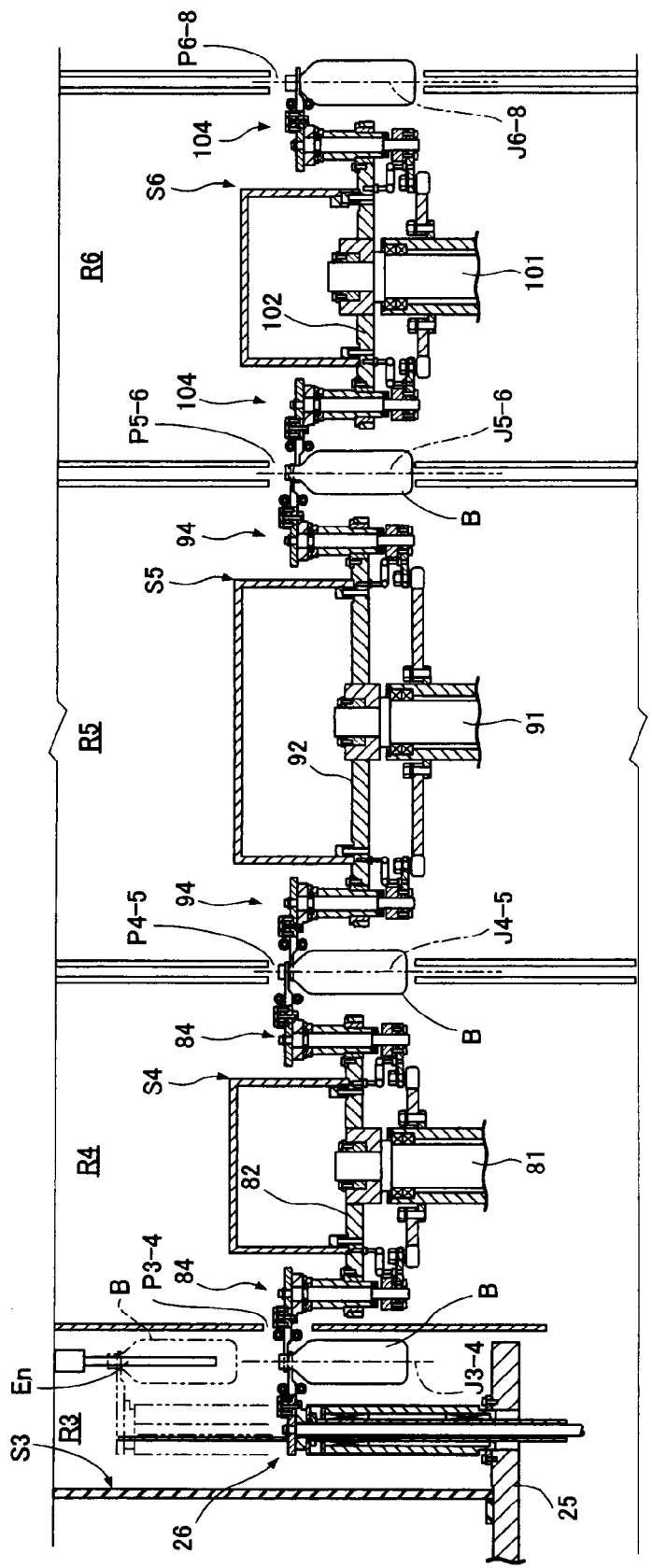
FIG. 8 is a longitudinal section showing the fourth to sixth revolving conveyors.
Figure 9:
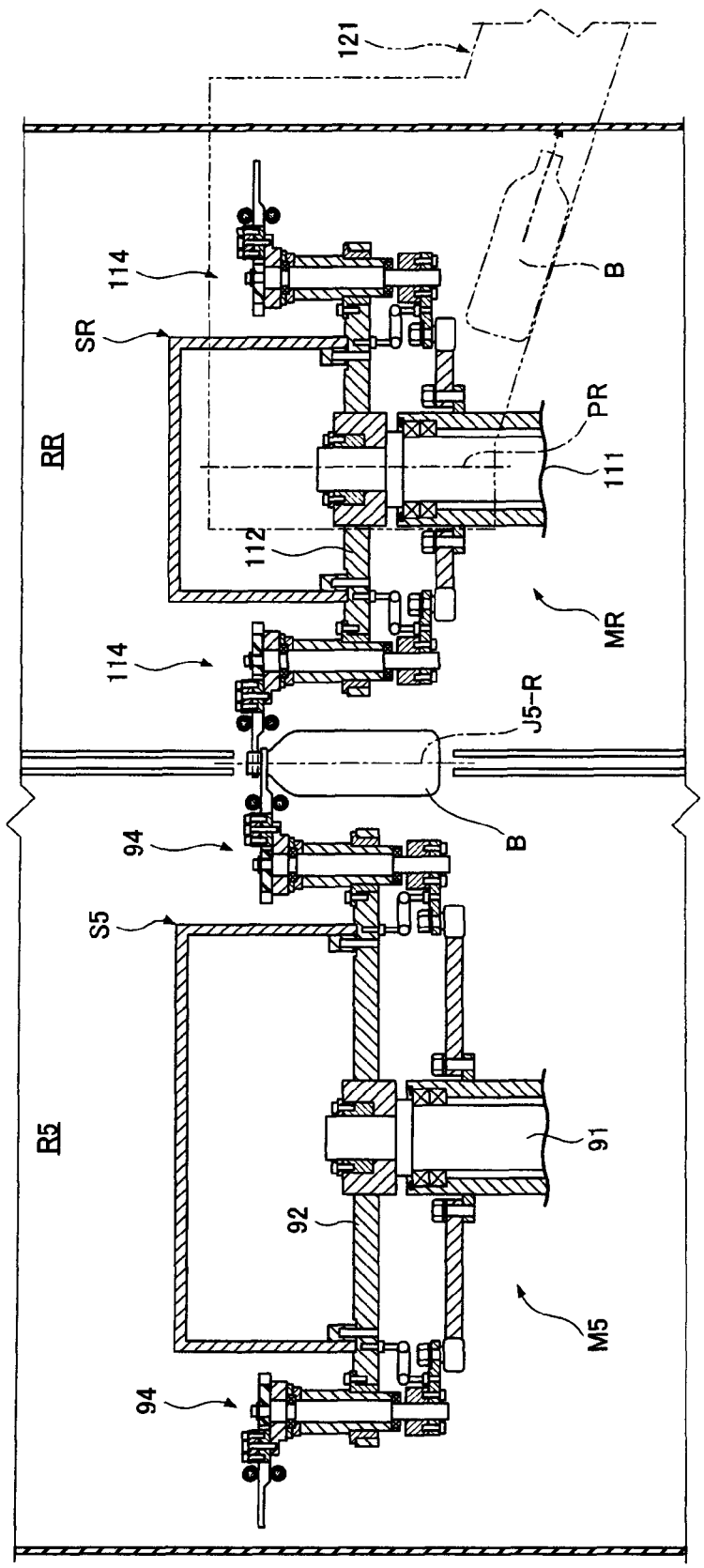
FIG. 9 is a longitudinal section showing the fifth revolving conveyor and the reject revolving conveyor.

As shown in FIGS. 6 and 7, the first container holder 54 includes a support cylinder 55 vertically penetrating the outer periphery of the first swiveling table 52, and a support plate 56 attached to the upper end of the support cylinder 55. A left and right pair of clamp arms 57a and 57b is supported on the support plate 56 so as to open and close via a pair of support pins 58. The clamp arms 57a and 57b can be opened and closed with respect to the support pin 58. Specifically, an interlock pin 60 attached to the one clamp arm 57a via a plate member is fit into a receiving groove on the other clamp arm 57b. The other clamp arm 57b can be opened and closed in synchronization with opening and closing of the one clamp arm 57a via the interlock pin 60. The interlock pin 60 is urged in a closing direction by a closing urging spring 59 connected between ends the clamp arms 57a and 57b.

An opening/closing shaft 61 is rotatably supported in the support cylinder 55, an opening/closing input cam follower 62 is attached to the lower end of the opening/closing shaft 61 via a cam lever, and an opening/closing restraint spring 63 connected to the cam lever brings the opening/closing input cam follower 62 into contact with opening/closing input cams 65 attached to the outer cylinder of the first rotating shaft 51 so as to coincide with a 0-1 joint J0-1 and a 1-2 joint J1-2 that transfer the containers B.

An opening/closing output cam 64 disposed between the proximal ends of the clamp arms 57a and 57b is attached to the upper end of the opening/closing shaft 61. The rotation of the opening/closing shaft 61 can open and close the clamp arm 57a through the opening/closing output cam 64.

First and second internal circumferential shields S1 and S2 are mounted on the respective inner peripheries of the first and second circular paths L1 and L2 on the first and second swiveling tables 52 and 72 of the first container holder 54 and the second container holder 74.

A first electron beam irradiator E1 disposed in the first shield chamber R1 and a second electron beam irradiator E2 disposed in a second shield chamber R2 will be described below.

If the outer surface of the container B is sterilized by electron beam irradiation, the first and second revolving conveyors M1 and M2 provided on the inner circumferences of the first and second circular paths L1 and L2 do not allow the installation of an electron beam irradiator. Thus, two electron beam irradiators are disposed on the respective outer peripheries of the two adjacent circular paths to emit electron beams to the two outer half surfaces of the container B.

In this case, important challenges are: A) to minimize the entry of contaminants into the outer-surface sterilization zone Z2 from the container B transported into the first shield chamber R1; B) to minimize the diffusion of contaminants to one of outer half surfaces of the container B from the other outer half surface before sterilization after the one outer half surface is sterilized, and minimize the contamination of the one sterilized outer half surface; and C) to minimize the recontamination of the container B to the inner-surface sterilization zone Z3 after the sterilization of the other outer half surface.

Hence, in order to attain A) in the first embodiment, the first electron beam irradiator E1 for emitting electron beams to the container B is located near the inlet of the first revolving channel L1, and sterilization on the outer surface of the container B is started with a minimum transport distance and a shortest time, thereby preventing the entry of contaminants from the container B.

In order to attain B), the first electron beam irradiator E1 is mounted on the first revolving channel L1 near the upstream side of the 1-2 joint J1-2 of the first revolving channel L1 and the second revolving channel L2, and the second electron beam irradiator E2 is mounted near the downstream side of the 1-2 joint J1-2 of the second revolving channel L2. This minimizes a transport distance and a time period from the sterilization of one outer half surface to the sterilization of the other outer half surface.

In order to attain C), the second revolving channel L2 is configured to maximize the irradiation of electron beams (X-rays) leaking into the container B. The electron beams are emitted from the second electron beam irradiator E2 in a carry-in channel L2c from a sterilization position on the other outer half surface to the 2-3 joint J2-3, and are emitted from the electron beam irradiation nozzle En of the outer-surface sterilization zone Z2 and leak through a 2-3 connecting opening (container entrance) P2-3.

Specifically, in the first shield chamber R1, the first electron beam irradiator E1 is mounted so as to emit electron beams to the container B, near the 0-1 joint J0-1 of the U-shaped feed channel LU and the first revolving channel L1 of the entrance trap zone Z1 and on the outer periphery of the first revolving channel L1 near the upstream side of the 1-2 joint J1-2. The second electron beam irradiator E2 is mounted on the outer periphery of the second revolving channel L2 near the downstream side of the 1-2 joint J1-2 in the second shield chamber R2. The direction of electron beam irradiation is set so as to emit electron beams from the second electron beam irradiator E2 to the container B on the second revolving channel L2 opposed to the second electron beam irradiator E2 and the container B on the carry-in channel L2c on the downstream side. Since the carry-in channel L2c faces the P2-3 connecting opening of the third shield chamber R3, electron beams (X-rays) leaking from the third shield chamber R3 are also emitted to the container B.

Figure 14:
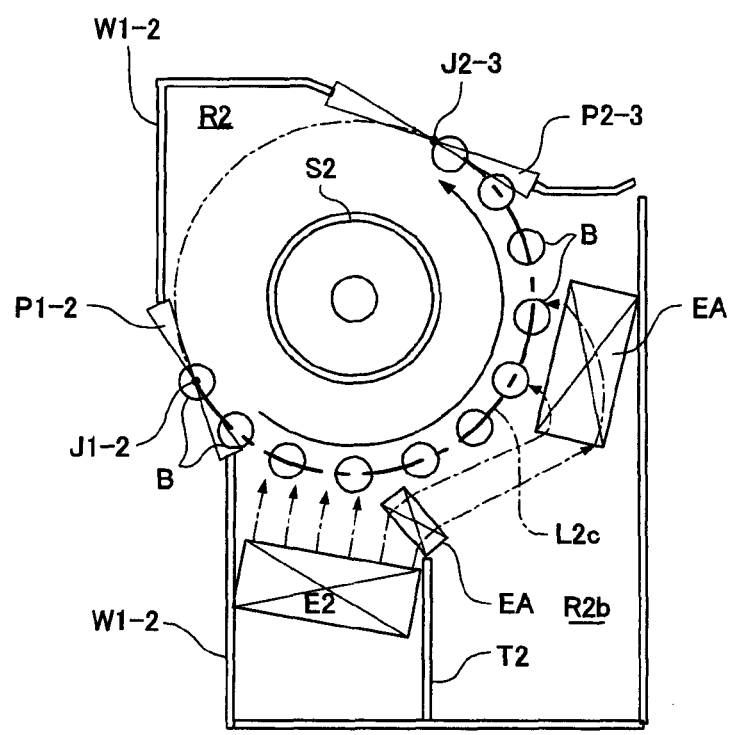
FIG. 14 is a plan view showing a variation of an electron beam irradiator including an electron beam deflector in a second shield chamber.

As shown in FIG. 14, some of electron beams emitted from the second electron beam irradiator E2 may be emitted to the container B on a carry-in channel L2b through at least one electron beam deflector EA after sterilization.

In the second shield chamber R2, a second chamber trap wall T2 composed of a metallic shield is protruded downstream of the second electron beam irradiator E2 toward the second revolving conveyor M2 from a shield wall R2a opposed to the 2-3 connecting opening P2-3 of the third shield chamber R3. The second chamber trap wall T2 forms a second attenuating chamber R2b. Thus, electron beams (X-rays) emitted from the 2-3 connecting opening P2-3 and the second electron beam irradiator E2 can be blocked by the second chamber trap wall T2 so as to be guided into the second attenuating chamber R2b. This attenuates the electron beams by reflection.

As shown in FIGS. 6 and 7, the neck n is transferred from the clamp arm 57b of the first container holder 54 to the clamp arm 57a of the second container holder 74 at the 1-2 joint J1-2. The clamp arm 57b of the first container holder 54 holds the neck n at a different position from the clamp arm 57a of the second container holder 74. Moreover, the first electron beam irradiator E1 emits electron beams to one outer half surface not held by the clamp arm 57b on the neck n, and then the second electron beam irradiator E2 emits electron beams to the other outer half surface not held by the clamp arm 57a on the neck n. Thus, the overall outer surface of the neck n can be sterilized in the outer-surface sterilization zone Z2.

(Entrance Trap Zone)

Figure 12A:
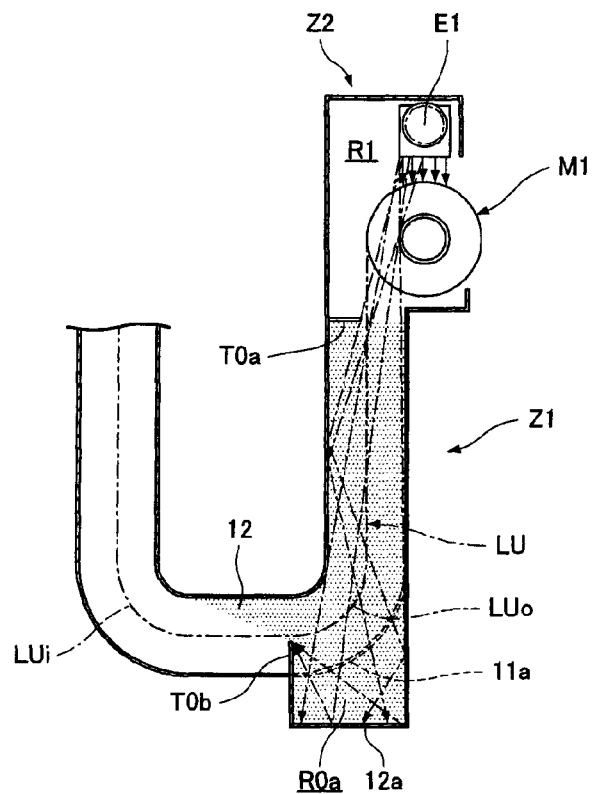
FIG. 12A is a cross section showing an entrance trap zone in plan view according to a first variation.

As shown in FIG. 12A, the entrance trap zone Z1 has a plurality of conveyor units 11 that form the U-shaped feed channel LU composed of two connected quarter arcs LUi and LUo in plan view, and an entrance trap shield chamber 12 shaped like a letter U in plan view so as to surround the U-shaped feed channel LU.

The entrance trap shield chamber 12 includes a plurality of first and second entrance trap walls T0a and T0b that are composed of metallic shields for shielding electron beams (X-rays) leaking from the outer surface and the inner-surface sterilization zones Z2 and Z3, and an entrance attenuating chamber R0a.

The first entrance trap wall T0a at the joint of the entrance trap shield chamber 12 and the first shield chamber R1 is protruded perpendicularly to the shield side wall of the entrance trap shield chamber 12 (in a crosswise direction) on the opposite side of the U-shaped feed channel LU from the first revolving channel L1. The first entrance trap wall T0a can reduce the entry of electron beams (X-rays) from the 0-1 connecting opening (container entrance) P0-1 into the entrance trap shield chamber 12 after the electron beams are emitted from the first electron beam irradiator E1, the second electron beam irradiator E2, and the electron beam irradiation nozzles En of the third shield chambers R3.

The first entrance attenuating chamber R0a on the downstream side is opposed to the first shield chamber R1 on the outer periphery of the quarter arc LUo on the downstream side. The first entrance attenuating chamber R0a is composed of a surrounding shield wall 12a that protrudes in a rectangular shape from the entrance trap shield chamber 12 in plan view. Reference numeral 11a denotes a not shielded conveyor shield wall provided on the opening of the first entrance attenuating chamber R0a so as to surround the conveyor unit 11. The first entrance attenuating chamber R0a reflects electron beams (X-rays) coming from the first shield chamber R1 through the 0-1 connecting opening P0-1, reducing a dose of radiation to the inlet of the entrance trap shield chamber 12.

The second entrance trap wall T0b on the upstream side is protruded from the upstream end of the first entrance attenuating chamber R0a in the crosswise direction of the U-shaped feed channel LU. Electron beams (X-rays) coming into the first entrance attenuating chamber R0a are blocked by the second entrance trap wall T0b, reducing a dose of radiation from the entrance trap shield chamber 12 to the entrance.

Figure 12B:
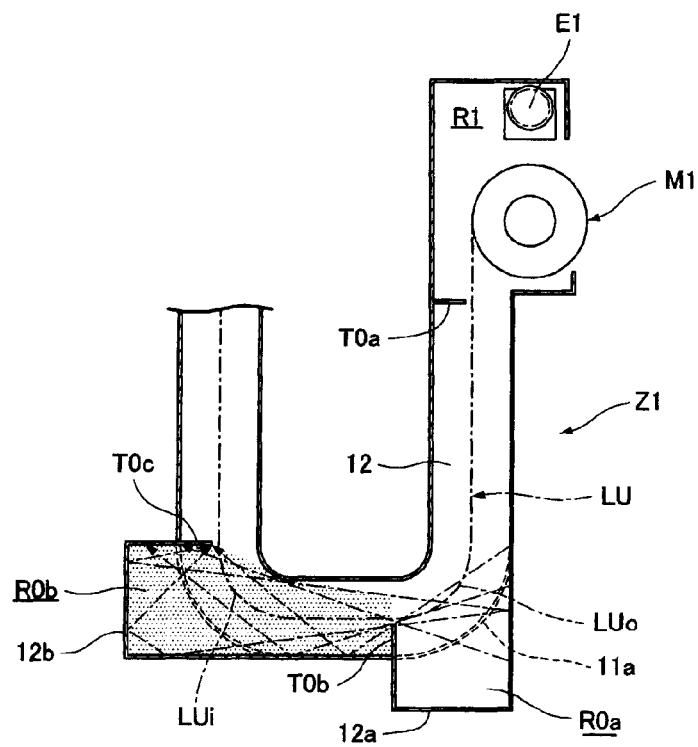
FIG. 12B is a cross section showing the entrance trap zone in plan view according to a second variation.

As shown in FIG. 12B, the entrance trap shield chamber 12 may further include a second entrance attenuating chamber R0b corresponding to the quarter arc LUi at the inlet, and a third entrance trap wall T0c. In this configuration, the second entrance attenuating chamber R0b and the third entrance trap wall T0c are formed by a surrounding shield wall 12b and are located on the outer periphery of the quarter arc LUi such that the second entrance attenuating chamber R0b and the third entrance trap wall T0c are rotated clockwise by 90° in plan view from the first entrance attenuating chamber R0a and the second entrance trap wall T0b. This can further considerably reduce a dose of radiation to the entrance of the entrance trap shield chamber 12.

(Exit Trap Zone)

In the exit trap zone Z4, the three fourth to sixth circular paths L4 to L6 formed by the fourth to sixth revolving conveyors M4 to M6 are connected in series from the 3-4 joint J3-4 on the exit side of the third revolving channel L3, are connected to a 6-8 joint J6-8 acting as a container ejecting part, and the fourth to sixth revolving conveyors M4 to M6 are stored in the respective fourth to sixth shield chambers R4 to R6 composed of metallic shields.

The fourth to sixth revolving conveyors M4 to M6 are mounted in the respective fourth to sixth shield chambers R4 to R6 on the base top plate 21U. The fourth to sixth revolving conveyors M4 to M6 have fourth to sixth rotating shafts 81, 91, and 101 that rotatably penetrate the base top plate 21U via bearings, and fourth to sixth swiveling tables 82, 92, and 102 that are fixed on the upper end of the fourth to sixth rotating shafts 81, 91, and 101. As shown in FIG. 5, a fourth interlock gear 83 engaged with the interlock third ring gear 48 of the third revolving conveyor M3 is attached to the lower end of the fourth rotating shaft 81, and a fifth interlock gear 93 engaged with the fourth interlock gear 83 is attached to the lower end of the fifth rotating shaft 91. Moreover, a sixth interlock gear 103 engaged with the fifth interlock gear 93 is attached to the lower end of the sixth rotating shaft 101. The fourth to sixth swiveling tables 82, 92, and 102 are rotated while being interlocked with the outer cylindrical shaft 23a of the third revolving conveyor M3.

The outer peripheries of the fourth to sixth swiveling tables 82, 92, and 102 have fourth to sixth container holders 84, 94, and 104 spaced at regular intervals. Moreover, fourth to sixth internal circumferential shields S4 to S6 are provided on the respective inner circumferences of the fourth to sixth circular paths L4 to L6 on the fourth to sixth swiveling tables 82, 92, and 102.

In this case, the fourth to sixth container holders 84, 94, and 104 are substantially identical to the first container holder 54 in structure except for the holding position of the neck n. Thus, the container holders are indicated by the same reference numerals and the explanation thereof is omitted.

The shield structure of the exit trap zone Z4 will be discussed below.

Figure 10A:
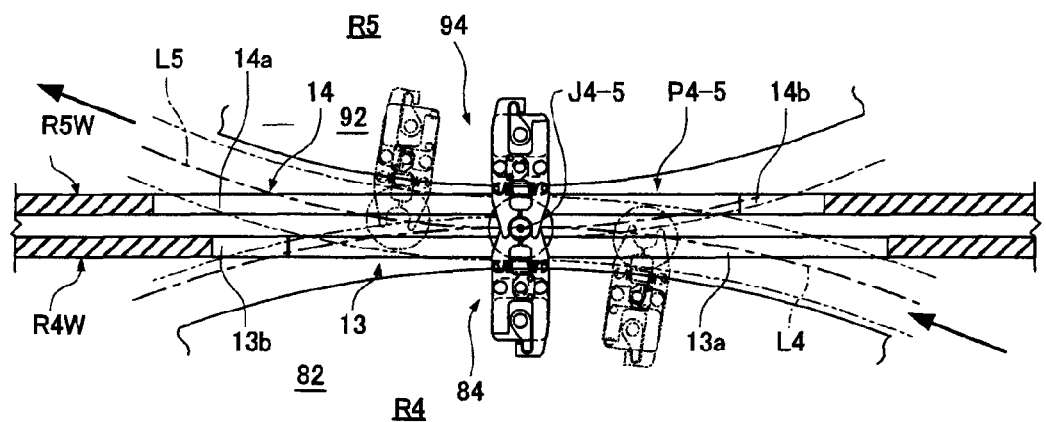
FIG. 10A is a cross section showing a 4-5 connecting opening in plan view.
Figure 10B:
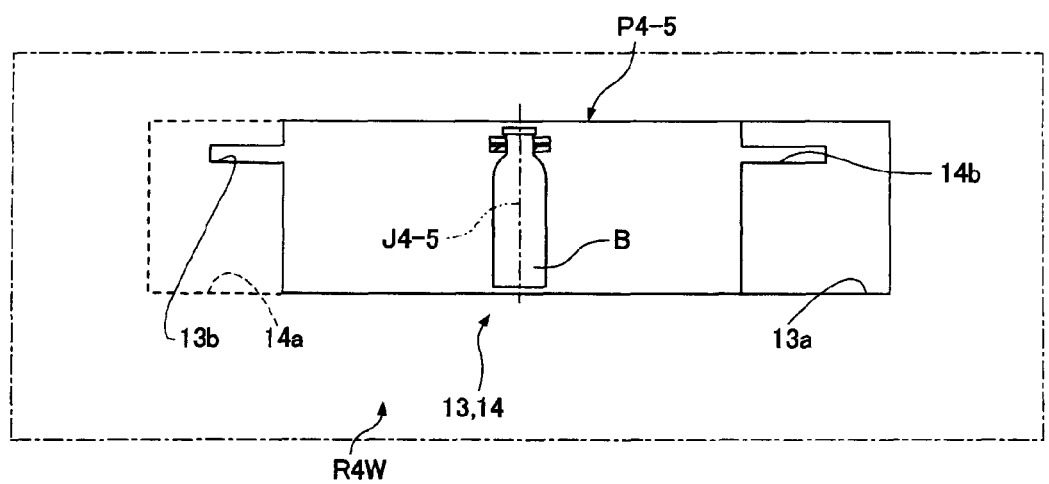
FIG. 10B is a front view showing the 4-5 connecting opening.

First, the 1-2 to 6-8 connecting openings P1-2 to P6-8 of the 1-2 to 6-8 joints J1-2 to J6-8 on the first to sixth circular paths L1 to L6 and a reject connecting opening P5-R of a reject joint J5-R on the reject revolving channel LR are substantially identical in structure. Thus, referring to FIGS. 10A and 10B, only a 4-5 connecting opening P4-5 formed at the 4-5 joint J4-5 will be discussed below and the explanation of the other connecting openings are omitted.

A shield side wall R4W of the fourth shield chamber R4 and a shield side wall R5W of the fifth shield chamber R5 are overlapped each other with a predetermined clearance. The 4-5 connecting opening P4-5 includes first and second openings 13 and 14 formed in odd shapes on the two respective shield side walls R4W and R5W. In other words, the first opening 13 includes a vertically long delivery part 13a that allows the passage of the container B transported on the fifth revolving channel L5 from the fourth revolving channel L4 through the 4-5 joint J4-5, and vertically the short holder insertion part 13b that allows the passage of the ends of the clamp arms 57a and 57b (35a, 35b) moved along the fifth revolving channel L5. The second opening 14 includes a delivery part 14a that allows the passage of the container B transported on the fifth revolving channel L5 from the fourth revolving channel L4 through the 4-5 joint J4-5, and a holder insertion part 14b that allows the passage of the ends of the clamp arms 57a and 57b (35a, 35b) moved along the fourth revolving channel L4. The first and second openings 13 and 14 in odd shapes are formed on the respective shield side walls R4W and R5W, thereby reducing a dose of electron beams (X-rays) leaking from the 4-5 connecting opening P4-5.

Figure 11A:
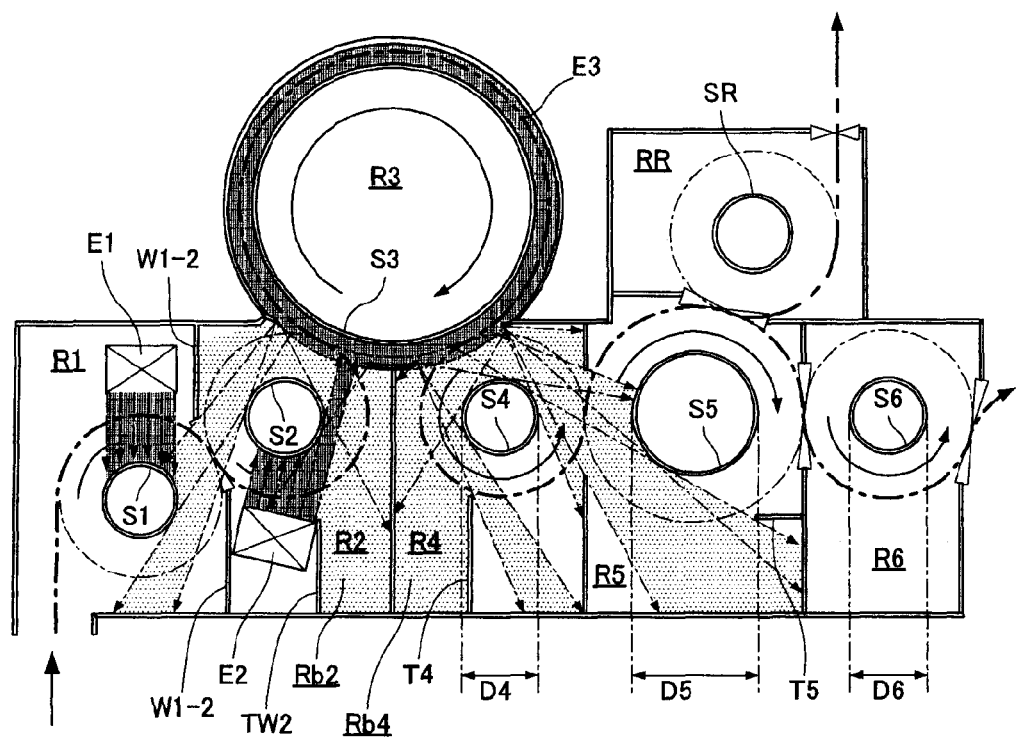
FIG. 11A is a plan view showing an irradiation region and a leakage region of electron beams (X-rays) in the electron beam sterilization equipment.

In the layout of the 4-5 to 6-8 joints J4-5 to J6-8 of the fourth to sixth circular paths L4 to L6, the 4-5 connecting opening P4-5 is disposed at an angle with respect to the 3-4 connecting opening P3-4; meanwhile, the 4-5 connecting opening P4-5, a 5-6 connecting opening P5-6, and the 6-8 connecting opening P6-8 are substantially linearly disposed and the fourth to sixth revolving conveyors M4 to M6 are substantially linearly disposed. As shown in FIG. 11A, electron beams directly leaking from the 3-4 connecting opening P3-4 of the third shield chamber R3 are detected substantially over the fourth shield chamber R4 but do not reach the back side where the electron beams are blocked by the fourth internal circumferential shield S4 of the fourth revolving conveyor M4. Electron beams reaching the fifth shield chamber R5 through the 4-5 connecting opening P4-5 are blocked by a fifth internal circumferential shield S5 of the fifth revolving conveyor M5 and do not reach the 5-6 connecting opening P5-6. Thus, it is understood that the fifth internal circumferential shield S5 quite effectively acts on electron beams reaching the fifth shield chamber R5.

Figure 11B:
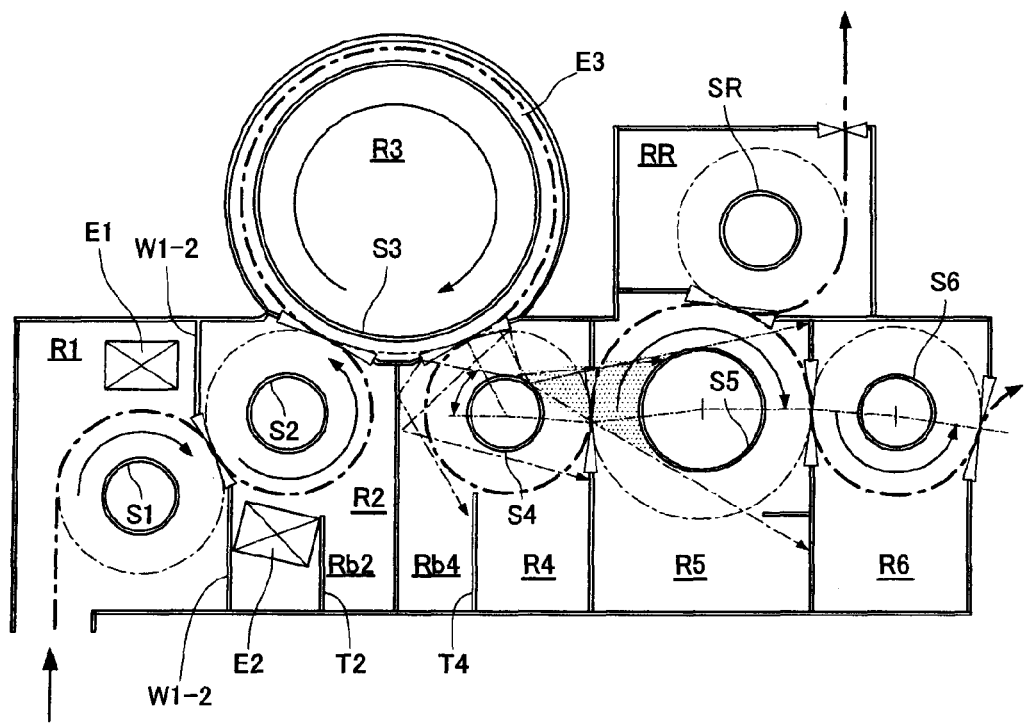
FIG. 11B is a plan view showing a reflected leakage region of electron beams (X-rays) in the electron beam sterilization equipment.

In this case, the outer diameter of the fifth revolving channel L5 is set larger than that of the fourth revolving channel L4, so that an outer diameter D5 of the fifth internal circumferential shield S5 of the fifth revolving conveyor M5 is larger than an outer diameter D4 of the fourth internal circumferential shield S4. This can effectively block electron beams (X-rays) leaking from the 3-4 connecting opening P3-4 and the 4-5 connecting opening P4-5. The outer diameter D5 of the fifth internal circumferential shield S5 is preferably 1.3 to 2.5 times larger than the outer diameter D4 of the fourth internal circumferential shield S4. If the outer diameter D5 is at least 1.3 times larger than the outer diameter D4, a remarkable shielding effect can be obtained. If the outer diameter D5 is 1 to 2.5 times larger than the outer diameter D4, a facility does not excessively increase in size. Regarding electron beams (X-rays) that leak from the 3-4 connecting opening P3-4 and collide with a metallic shield, as shown in FIG. 11B, if X-rays generated by collision with the fourth internal circumferential shield S4 from the 3-4 connecting opening P3-4 leak into the fifth shield chamber R5 through the 4-5 connecting opening P4-5, the X-rays may leak into the sixth shield chamber R6 through the 5-6 connecting opening P5-6 as the outer diameter D5 of the fifth internal circumferential shield S5 decreases. Though, an X-ray dosage leaking from the 5-6 connecting opening P5-6 into the sixth shield chamber R6 can be substantially eliminated by increasing the outer diameter D5 of the internal circumferential shield S5.

In the fourth shield chamber R4, a fourth chamber trap wall T4 composed of a metallic shield is protruded toward the 3-4 connecting opening P3-4 from a shield wall R4a opposed to the 3-4 connecting opening P3-4 of the third shield chamber R3. The fourth chamber trap wall T4 forms a fourth attenuating chamber R4b. Thus, electron beams (X-rays) leaking from the electron beam irradiation nozzle En of the third shield chamber R3 to the fourth shield chamber R4 through the 3-4 connecting opening P3-4 can be blocked by the fourth chamber trap wall T4 so as to be guided into the fourth attenuating chamber R4b. This attenuates the electron beams by reflection.

The fifth shield chamber R5 contains a fifth chamber trap wall T5 substantially vertically protruded from the shield side wall near the 5-6 connecting opening P5-6. The fifth chamber trap wall T5 is located on the opposite side of the 5-6 connecting opening P5-6 from the reject chamber RR. The fifth chamber trap wall T5 can reduce a dose of radiation from the 5-6 connecting opening P5-6 into the sixth shield chamber R6 by reflecting electron beams (X-rays) on the shield wall after the electron beams enter from the 4-5 connecting opening P4-5.

[Reject Zone]

For the reject zone ZR for ejecting the insufficiently sterilized container B when a predetermined electron dose is not obtained, for example, at a low supplied voltage, the reject revolving conveyor MR is mounted in a clean room 22 and the reject revolving channel LR is formed. In the reject revolving conveyor MR, a reject rotating shaft 111 penetrates the base top plate 21U via a bearing, and a reject swiveling table 112 is attached to the upper end of the reject rotating shaft 111. On the outer periphery of the reject swiveling table 112, reject container holders 114 identical in structure to the first container holder 54 are attached at regular intervals. The reject interlock gear 113 attached to the lower end of the reject rotating shaft 111 is engaged with the fifth interlock gear 93, allowing the reject swiveling table 112 to rotate while being interlocked with the outer cylindrical shaft 23a of the third revolving conveyor M3.

Figure 13A:
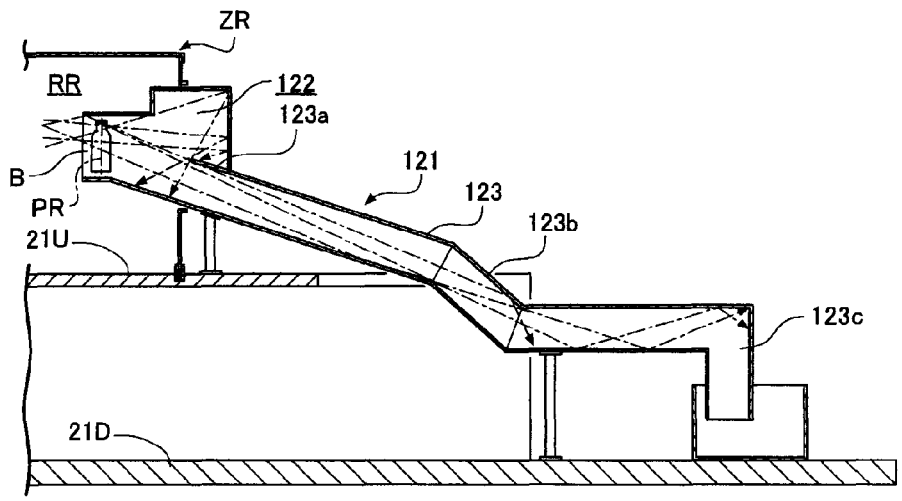
FIG. 13A is a longitudinal section showing a container exit chute of a reject zone according to a first modification.
Figure 13B:
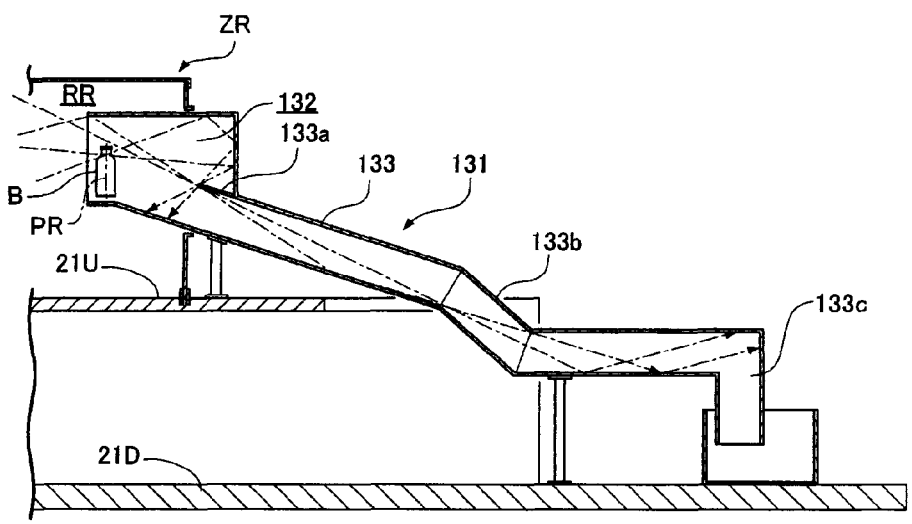
FIG. 13B is a longitudinal section showing a container exit chute of the reject zone according to a second modification.
Figure 13C:
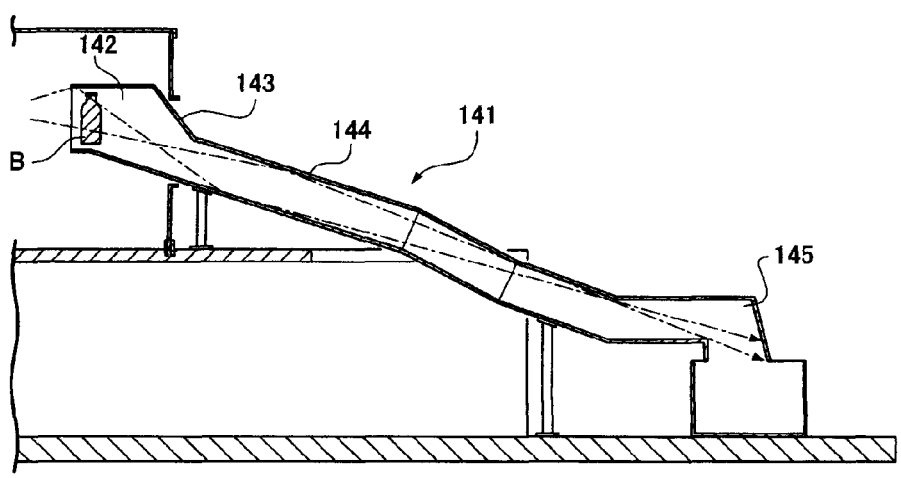
FIG. 13C is a longitudinal section showing a typical container exit chute of the reject zone.

Referring to FIGS. 13A to 13C, exist chutes 121 and 131 mounted on the reject revolving channel LR in the reject zone ZR will be described below.

FIG. 13C shows an exit chute 141 in a typical example. In this structure, the container B is fed into a tilted chute body 144 through a ceiling tapered part 143 from a container entrance 142 formed so as to correspond to the reject ejection port PR, and then the container B is dropped into a tray from a container exit 145. In the case of the exit chute 141, X-rays at the reject ejection port PR with fewer reflections are likely to leak directly from the container exit 145.

FIG. 13A shows a first modification of the exit chute 121 formed by a metallic shield wall. In the reject shield chamber RR downstream of the reject ejection port PR, an attenuating chamber 122 having a high ceiling is formed with a step, and an entrance ceiling 123a of the chute body 123 is protruded into the attenuating chamber 122. A bent part 123b is formed at an intermediate part of the chute body 123, and the container exit 123c is bent downward. In the exit chute 121, X-rays are reflected on the shield wall of the attenuating chamber 122 and then are reflected on the bent part 123b and the shield wall of the container exit 123c. This considerably reduces an X-ray dose leaking from the container exit 123c.

FIG. 13B shows a second modification of the exit chute 131 formed by a metallic shield wall. An attenuating chamber 132, an entrance part 133a, a bent part 133b, and a container exit 133c are formed as in the first modification. The second modification is different from the first modification in that the ceiling part of the attenuating chamber 132 has a flat surface instead of a step. The exit chute 131 of the second modification can obtain the same effect as the first modification.

Effect of the First Embodiment

According to the first embodiment, the first and second electron beam irradiators E1 and E2 for sterilizing the outer half surfaces of the container B by electron beam radiation are located close to each other near the upstream side and the downstream side of the 1-2 joint J1-2 of the first and second circular paths L1 and L2 located in the outer-surface sterilization zone Z2. Thus, the other outer half surface can be sterilized in a short time after the sterilization of the one outer half surface. This can considerably reduce recontamination on one outer half surface by contaminants from the other outer half surface, thereby effectively sterilizing the overall outer surface.

Some electron beams from the second electron beam irradiator E2 are emitted to the container B on the second revolving channel L2 after sterilization, thereby effectively preventing recontamination on the overall sterilized outer surface of the container B.

In the outer-surface and inner-surface sterilization zones Z2 and Z3, the first to third internal circumferential shields S1 to S3 are mounted along the internal circumferences of the first to third circular paths L1 to L3 in the first to third revolving units M1 to M3. Thus, the number of reflections of electron beams is increased between the first to third shield chambers R1 to R3 and the first to third internal circumferential shields S1 to S3 of the outer-surface and inner-surface sterilization zones Z2 and Z3, achieving effective attenuation.

In the exit trap zone Z4, the fourth to sixth internal circumferential shields S4 to S6 are mounted along the internal circumferences of the fourth to sixth circular paths L4 to L6 in the fourth to sixth revolving units M4 to M6. This can effectively block electron beams (X-rays) leaking from the third shield chamber R3 of the inner-surface sterilization zone Z3 through the 3-4 connecting opening P3-4, thereby effectively attenuating electron beams (X-rays) leaking downstream.

Furthermore, in the inner-surface sterilization zone Z3, in order to insert the electron beam irradiation nozzle En into the inlet of the container B and emit electron beams, the container B needs to be transported with a sufficient distance and time. Thus, an extension of the third revolving channel L3 requires a larger diameter. As the fourth revolving channel L4 of the exit trap zone Z4 disposed at the 3-4 connecting opening P3-4 increases in diameter, the transport distance of the third revolving channel L3 is limited. Thus, the fourth revolving channel L4 cannot have a large diameter in the exit trap zone Z4. This necessarily tends to increase an electron beam (X-ray) dose leaking from the 3-4 connecting opening P3-4 to the fourth shield chamber R4 upstream of the exit trap zone Z4.

To address this problem, the outer diameter D5 of the fifth revolving channel L5 is set larger than the outer diameter D4 of the fourth internal circumferential shield S4. Preferably, the outer diameter D5 of the fifth internal circumferential shield S5 is 1.3 to 2.5 times larger than the outer diameter D4 of the fourth internal circumferential shield S4. This can effectively reduce an electron beam (X-ray) dose leaking downstream from the fourth shield chamber R4 through the fifth shield chamber R5.

In the fourth shield chamber R4 of the exit trap zone Z4, the fourth chamber trap wall T4 is provided to form the fourth attenuating chamber R4b. Thus, electron beams (X-rays) leaking from the 3-4 connecting opening P3-4 of the inner-surface sterilization zone Z3 can be introduced into the fourth attenuating chamber R4b and thus can be effectively reflected and attenuated in the fourth attenuating chamber R4b.

In the fifth shield chamber R5, the fifth chamber trap wall T5 is provided on the shield side wall near the 5-6 connecting opening P5-6. This blocks electron beams (X-rays) coming from the 4-5 connecting opening P4-5, reducing a dose of radiation into the sixth shield chamber R6.

In the second shield chamber R2 of the outer-surface sterilization zone Z2, the second attenuating chamber R2b is formed by the second chamber trap wall T2 protruding from the shield wall opposed to the 2-3 connecting opening P2-3. Thus, electron beams (X-rays) leaking from the 2-3 connecting opening P2-3 are introduced into the second attenuating chamber R2b by the second chamber trap wall T2, and thus the electron beams can be effectively reflected and attenuated.

Second Embodiment

Figure 15:
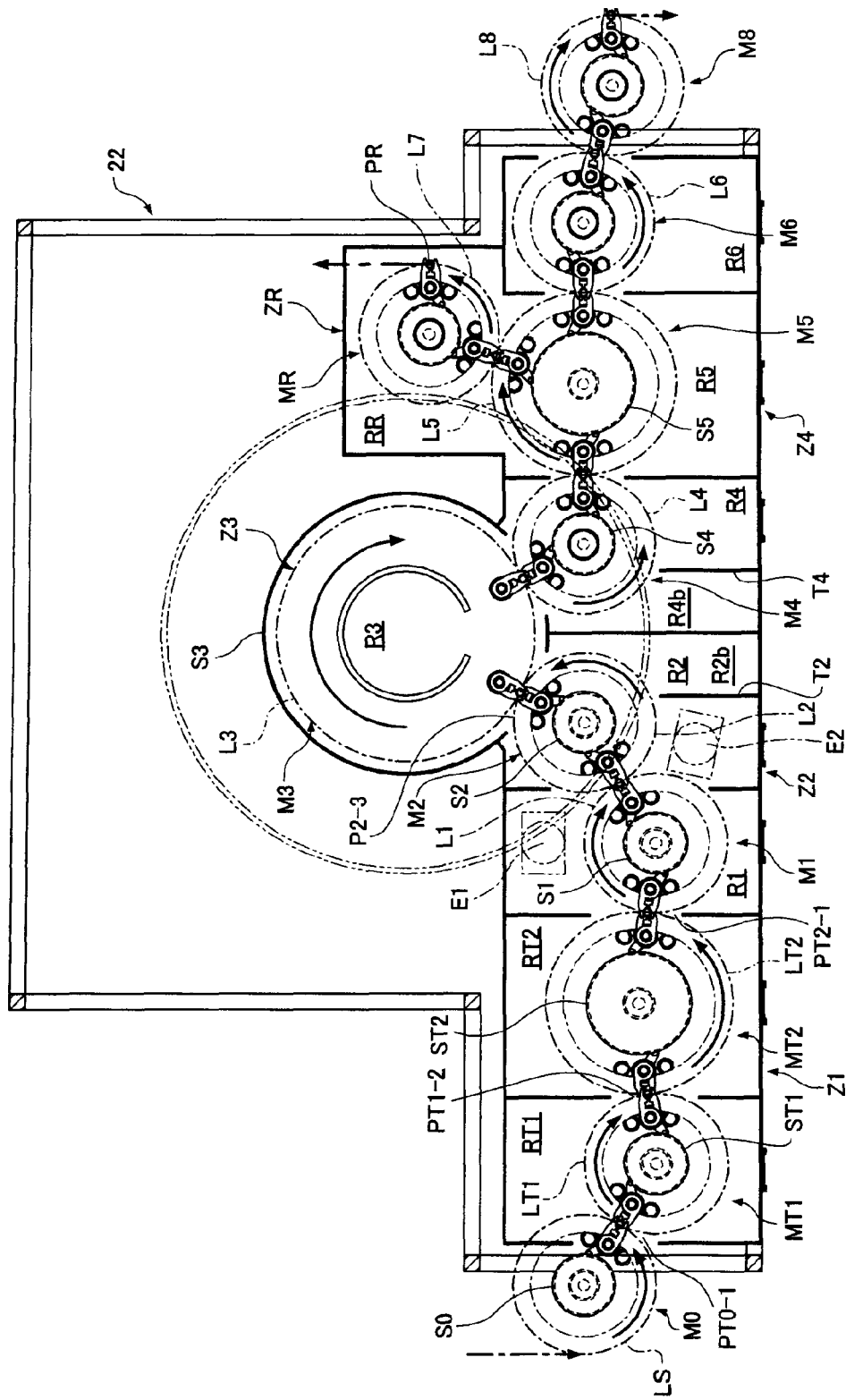
FIG. 15 is a cross section showing a second embodiment of electron beam sterilization equipment in plan view according to the present invention.
Figure 16A:
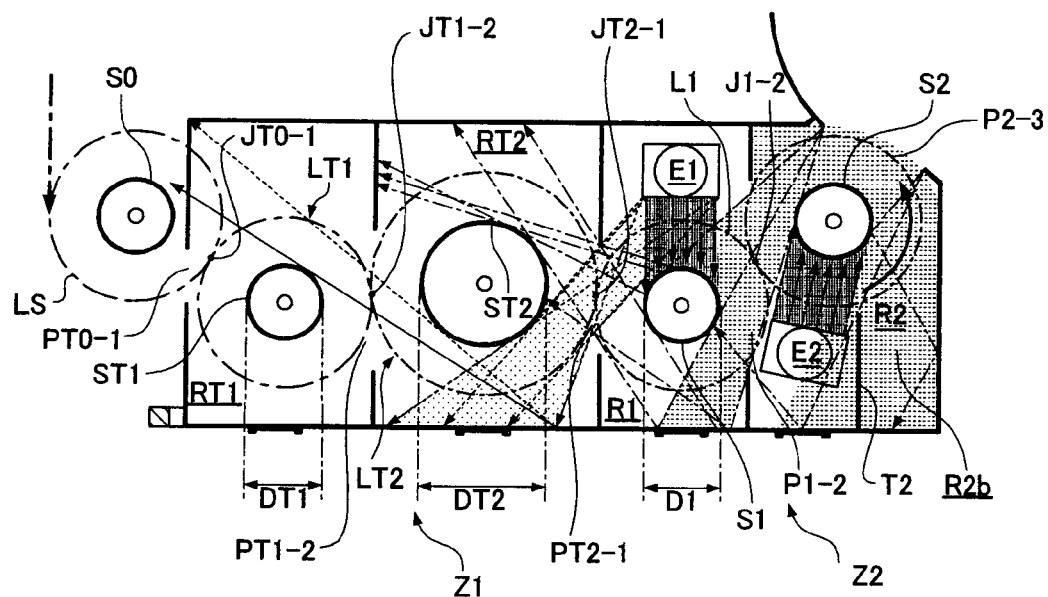
FIG. 16A is a plan view showing an irradiation region and a leakage region of electron beams in an entrance trap zone.
Figure 16B:
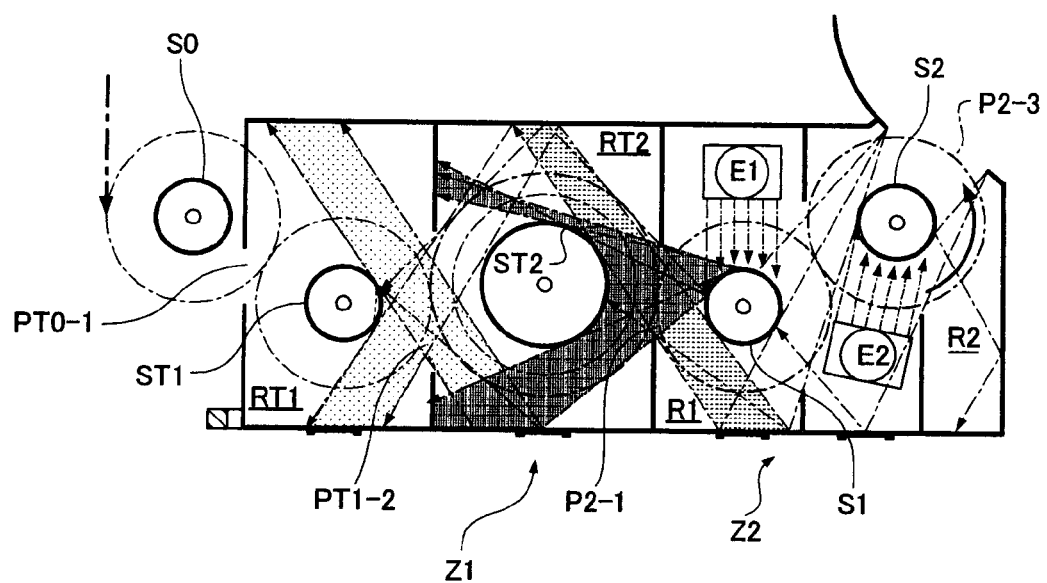
FIG. 16B is a plan view showing a reflected X-ray leakage region of electron beams in an entrance trap zone.

Referring to FIGS. 15, 16A and 16B, a second embodiment of electron beam sterilization equipment according to the present invention will be described below. In the second embodiment, an entrance trap zone Z1 includes a plurality of circular paths LT1 and LT2.

In the entrance trap zone Z1, the first trap revolving channel LT1 and the second trap revolving channel LT2 are connected in series between a first revolving channel L1 and a carry-in revolving channel LS formed by a carry-in revolving conveyor M0. Moreover, a first trap revolving conveyor MT1 forming the first trap revolving channel LT1 and a second trap revolving conveyor MT2 forming the second trap revolving channel LT2 are respectively stored in a first trap shield chamber RT1 and a second trap shield chamber RT2 that are formed by metallic shield walls. In the carry-in revolving conveyor M0 and the first and second trap revolving conveyors MT1 and MT2, a carry-in part internal circumferential shield wall S0 and first and second trap internal circumferential shield walls ST1 and ST2, which are composed of metallic shield walls, are provided along the internal circumferences of the circular paths LS, LT1, and LT2. Furthermore, on the shield walls of the first trap shield chamber RT1 and the second trap shield chamber RT2, a trap entrance PT0-1, a trap intermediate PT1-2, and a trap exit connecting opening PT2-1 substantially identical in structure to those of the first embodiment are respectively formed at a trap entrance joint JT0-1 of the carry-in revolving channel LS and the first trap revolving channel LT1, a trap intermediate joint JT1-2 of the first trap revolving channel LT1 and the second trap revolving channel LT2, and a trap exit joint JT2-1 of the second trap revolving channel LT2 and the first revolving channel L1.

The carry-in revolving unit M0 and the first and second trap revolving conveyors MT1 and MT2 are identical in configuration to those of the first embodiment. Thus, the carry-in revolving unit M0 and the first and second trap revolving conveyors MT1 and MT2 are indicated by the same reference numerals and the explanation thereof is omitted.

As shown in FIGS. 16A and 16B, electron beams emitted from the electron beam irradiation nozzle En of the third shield chamber R3 and the second electron beam irradiator E2 hardly enter the second trap shield chamber RT2 directly or as reflected X-rays. However, electron beams emitted from the first electron beam irradiator E1 may leak into the second trap shield chamber RT2 from the trap exit connecting opening PT2-1. To address this problem, the outer diameter of the second trap revolving channel LT2 is larger than that of the first revolving channel L1, and an outer diameter DT2 of the second trap internal circumferential shield ST2 is larger than an outer diameter D1 of the first internal circumferential shield S1. The second trap internal circumferential shield ST2 facing the trap exit connecting opening PT2-1 is so large as to effectively block electron beams (X-rays) leaking from the trap exit connecting opening PT2-1. Preferably, the outer diameter DT2 of the second trap internal circumferential shield ST2 is 1.3 to 2.5 times larger than the outer diameter D1 of the first internal circumferential shield S1. If the outer diameter DT2 is at least 1.3 times larger than the outer diameter D1, a remarkable shielding effect can be obtained. If the outer diameter DT2 is 1 to 2.5 times larger than the outer diameter D1, a facility does not excessively increase in size.

In FIGS. 15, 16A and 16B, one shield wall of the trap entrance connecting opening PT0-1 of the first trap shield chamber RT1 is extended because the shield wall has an opening only for the insertion of a container holder.

(Variations of the Internal Circumferential Shield)

Figure 17A:
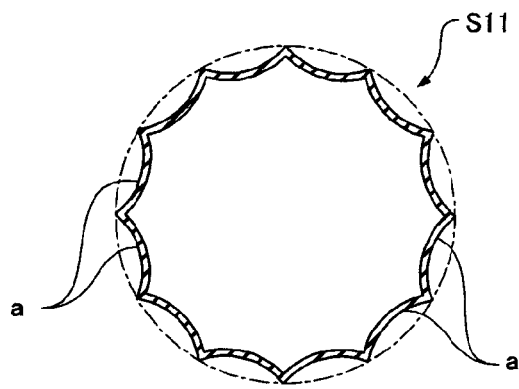
FIG. 17A is a cross section showing a variation of an internal circumferential shield in plan view.
Figure 17B:
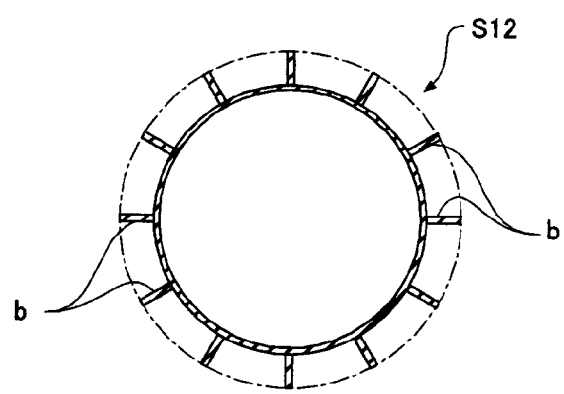
FIG. 17B is a cross section showing a variation of an internal circumferential shield in plan view.
Figure 17C:
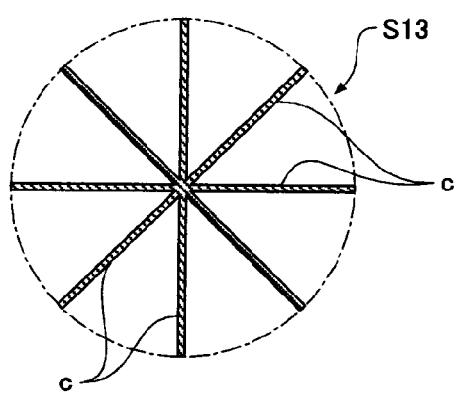
FIG. 17C is a cross section showing a variation of an internal circumferential shield in plan view.

In the first and second embodiments, the first to sixth internal circumferential shields S1 to S6, the intermediate internal circumferential shield S8, the reject internal circumferential shield SR, the carry-in internal circumferential shield S0, and the first and second trap internal circumferential shields ST1 and ST2 are shaped like cylinders with closed top surfaces in the first to sixth revolving conveyors M1 to M6, the intermediate revolving conveyor M8, the reject revolving conveyor MR, the carry-in revolving conveyor M0, and the first and second trap revolving conveyors MT1 and MT2. Like an internal circumferential shield S11 in FIG. 17A, grooves a formed in the axial direction may be circumferentially spaced at regular intervals on the outer periphery shaped cylindrically. Like an internal circumferential shield S12 in FIG. 17B, reflecting plates b protruded along the axial direction may be circumferentially spaced at regular intervals on the outer periphery of the cylinder. Like the internal circumferential shield S13 in FIG. 17C, shield plates c crossing one another at the axis may be radially assembled at a predetermined angle.

The internal circumferential shields S11 to S13 can more effectively diffuse incident electron beams so as to accelerate attenuation.

The invention claimed is:

1. A shield structure for electron beam sterilization, the shield structure comprising:
a plurality of shield chambers each containing each one of a plurality of circular paths connected in series, wherein containers are transported along with the circular paths; and a sterilization zone including an outer-surface sterilization zone in which an outer surface of the container is sterilized by emitting electron beams to the container from electron beam irradiators disposed outside first and second circular paths upstream in a container transporting direction, and an inner-surface sterilization zone in which an electron beam irradiation nozzle is inserted into the container transported along a third circular path downstream in the container transporting direction, and thereby electron beams are emitted to sterilize an inner surface of the container, wherein
the sterilization zone has a container entrance where an entrance trap zone for attenuating electron beams is connected and a container exit where an exit trap zone for attenuating electron beams is connected, at least one of the entrance trap zone and the exit trap zone includes more than two of the plurality of circular paths connected in series, and two or more of the plurality of shield chambers containing the respective two or more of the plurality of circular paths, a sterilization zone internal circumferential shield composed of a metallic shield is mounted along an internal circumference of each of the circular paths in the sterilization zone, a trap zone internal circumferential shield composed of a metallic shield is mounted on two or more of the plurality of the circular paths in the entrance trap zone or the exit trap zone along the internal circumference of the circular path, and the shield structure satisfies at least one of conditions (I) and (II):

(I) the circular paths in the exit trap connected to the inner-surface sterilization zone include a first upstream circular path and a first downstream circular path connected to the first upstream circular path, and the internal circumferential shield of the first downstream circular path has a larger outer diameter than an outer diameter of the internal circumferential shield of the first upstream circular path, (II) the circular paths in the entrance trap zone connected to the outer-surface sterilization zone include a second upstream circular path and a second downstream circular path connected to the second upstream circular path, and the internal circumferential shield of the second downstream circular path has a larger outer diameter than an outer diameter of the internal circumferential shield of the second upstream circular path.

2. The shield structure for electron beam sterilization according to claim 1, wherein the internal circumferential shield of the first downstream circular path has an outer diameter 1.3 to 2.5 times larger than the outer diameter of the internal circumferential shield of the first upstream circular path in the exit trap zone.

3. The shield structure for electron beam sterilization according to claim 1, wherein the internal circumferential shield of the second downstream circular path has an outer diameter 1.3 to 2.5 times larger than the outer diameter of the internal circumferential shield of the second upstream circular path in the entrance trap zone.

4. The shield structure for electron beam sterilization according to claim 1, wherein in the exit trap zone, a first shield chamber containing a most upstream circular path has a first attenuating chamber opened to the container exit of the inner-surface sterilization zone, the first attenuating chamber being formed by dividing the first shield chamber by a first trap wall protruding forward to the container exit from a shield wall of the first shield chamber opposed to the container exit.

5. The shield structure for electron beam sterilization according to claim 1, wherein in the outer-surface sterilization zone, a second shield chamber containing a most downstream circular path has a second attenuating chamber opened to the container entrance of the inner-surface sterilization zone, the second attenuating chamber being formed by dividing the second shield chamber by a second trap wall protruding forward to the container entrance from a shield wall of the second shield chamber opposed to the container entrance.

* * * * *

UNITED STATES PATENT AND TRADEMARK OFFICE
CERTIFICATE OF CORRECTION

Page 1 of 1

PATENT NO. : 8,853,654 B2
APPLICATION NO. : 14/351177
DATED : October 7, 2014
INVENTOR(S) : Takayasu Yokobayashi, Satoshi Ogawa and Toru Hosokawa It is certified that error appears in the above-identified patent and that said Letters Patent is hereby corrected as shown below:

In the Claims

Column 17, lines 31-32, Claim 1, "the second upstream circular path" should read --an upstream circular path of the outer-surface sterilization zone--.

Signed and Sealed this
Eighth Day of September, 2015

Michelle K. Lee
*Director of the United States Patent and Trademark Office*